(12) United States Patent
Terada et al.

(10) Patent No.: US 10,508,078 B2
(45) Date of Patent: Dec. 17, 2019

(54) COMPOUND, PHOTOPOLYMERIZATION INITIATOR COMPRISING SAID COMPOUND, AND PHOTOSENSITIVE RESIN COMPOSITION CONTAINING SAID PHOTOPOLYMERIZATION INITIATOR

(71) Applicants: TOKYO UNIVERSITY OF SCIENCE FOUNDATION, Tokyo (JP); NIPPON KAYAKU KABUSHIKI KAISHA, Tokyo (JP)

(72) Inventors: Kiwamu Terada, Saitama (JP); Kazuyoshi Yamamoto, Tokyo (JP); Koji Arimitsu, Tokyo (JP)

(73) Assignees: TOKYO UNIVERSITY OF SCIENCE FOUNDATION, Tokyo (JP); NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/781,623

(22) PCT Filed: Dec. 7, 2016

(86) PCT No.: PCT/JP2016/086401
§ 371 (c)(1),
(2) Date: Jun. 5, 2018

(87) PCT Pub. No.: WO2017/099130
PCT Pub. Date: Jun. 15, 2017

(65) Prior Publication Data
US 2018/0370908 A1 Dec. 27, 2018

(30) Foreign Application Priority Data

Dec. 9, 2015 (JP) ................................. 2015-240433
Jun. 24, 2016 (JP) ................................. 2016-126097

(51) Int. Cl.
*C07C 271/24* (2006.01)
*C08F 2/50* (2006.01)
(Continued)

(52) U.S. Cl.
CPC .......... *C07C 271/24* (2013.01); *C07C 269/02* (2013.01); *C08F 2/50* (2013.01); *C08K 5/205* (2013.01); *C08L 63/00* (2013.01); *G03F 7/0045* (2013.01); *G03F 7/031* (2013.01); *G03F 7/038* (2013.01); *G03F 7/0385* (2013.01); *G03F 7/0387* (2013.01); *G03F 7/2037* (2013.01)

(58) Field of Classification Search
CPC ... C07C 269/02; C07C 271/24; C07C 271/12; C08F 2/50; C08K 5/205; C08L 63/00; G03F 7/004; G03F 7/031; G03F 7/2037; G03F 7/0045; G03F 7/038; G03F 7/0385; G03F 7/0387; C09D 7/40
See application file for complete search history.

(56) References Cited

U.S. PATENT DOCUMENTS

| 2004/0258921 A1 | 12/2004 | Watanabe et al. |
| 2007/0021524 A1 | 1/2007 | Watanabe et al. |
| 2012/0202158 A1 | 8/2012 | Hatakeyama et al. |

FOREIGN PATENT DOCUMENTS

| JP | 2004-163764 A | 6/2004 |
| JP | 2004-163765 A | 6/2004 |

(Continued)

OTHER PUBLICATIONS

Ishikawa et al., "Development of Photobase Generator with Benzoin Derivatives and Its Application to Photosensitive Materials," Chem. Lett. 2014, 43, 612-614. (Year: 2014).*

(Continued)

*Primary Examiner* — Yevgeny Valenrod
*Assistant Examiner* — Blaine G Doletski
(74) *Attorney, Agent, or Firm* — Greenblum & Bernstein, P.L.C.

(57) ABSTRACT

The purpose of the present invention is to provide: a novel compound which can generate a base and radical upon the irradiation with an active energy ray; a photopolymerization initiator which comprises the novel compound; and a photosensitive resin composition which contains the photopolymerization initiator, has high sensitivity and excellent storage stability, and can be formed into a cured article that does not have a metal-corrosive property. The novel compound is represented by formula (1):

(1)

[Chemical structure showing a compound with two substituted phenyl rings bearing substituents $R_2, R_3, R_4, R_5, R_6$, connected through a central carbon bearing $R_1$ and a carbonyl group, with a $-CH_2-O-C(=O)-NH-X$ linkage, enclosed in brackets with subscript $n$.]

(wherein $R_1$ to $R_6$ independently represent a hydrogen atom, a hydroxy group, an alkoxy group, an organic group other than the aforementioned substituents, or the like; X represents a residue having a structure such that n hydrogen atoms are removed from a saturated hydrocarbon containing a ring structure; and n represents an integer of 1 to 6).

10 Claims, 2 Drawing Sheets

(51) Int. Cl.
  *G03F 7/031* (2006.01)
  *C07C 269/02* (2006.01)
  *C08K 5/205* (2006.01)
  *C08L 63/00* (2006.01)
  *G03F 7/20* (2006.01)
  *G03F 7/004* (2006.01)
  *G03F 7/038* (2006.01)

(56) References Cited

FOREIGN PATENT DOCUMENTS

| JP | 2004-163766 A | 6/2004 |
| JP | 2006-023580 A | 1/2006 |
| JP | 2006-023581 A | 1/2006 |
| JP | 2006-023582 A | 1/2006 |
| JP | 2012-018197 A | 1/2012 |
| JP | 2012-018198 A | 1/2012 |
| JP | 2012-082247 A | 4/2012 |
| JP | 2012-181510 A | 9/2012 |
| JP | 2015-110765 A | 6/2015 |
| WO | 02/092718 A1 | 11/2002 |

OTHER PUBLICATIONS

Nobuhiro Ishikawa et al., "Photosensitivity Characteristics of UV Curable Organic-Inorganic Hybrids Sensitized with Benzoin Derivatives as Photobase Generators", Journal of Photopolymer Science and Technology, vol. 27, No. 2, (2014), pp. 223-225.

Koji Arimitsu et al., "Kobunshi Ronbushu", Japanese Journal of Polymer Science and Technology, vol. 71, No. 2, Feb. 25, 2014, pp. 53-58.

International Search Report issued with respect to Patent Application No. PCT/JP2016/086401, dated Jan. 24, 2017.

International Preliminary Report on Patentability issued with respect to Patent Application No. PCT/JP2016/086401, dated Jan. 15, 2018.

* cited by examiner

[Figure 1]

COMPOUND, PHOTOPOLYMERIZATION INITIATOR COMPRISING SAID COMPOUND, AND PHOTOSENSITIVE RESIN COMPOSITION CONTAINING SAID PHOTOPOLYMERIZATION INITIATOR

TECHNICAL FIELD

The present invention relates to a novel compound, a photopolymerization initiator containing the compound which generates bases and radicals by irradiation of active energy ray, and a photosensitive resin composition containing the photopolymerization initiator.

BACKGROUND ART

A photoacid generator generating a strong acid by irradiation of active energy ray such as light, infrared rays, electron beam or X-ray, and a chemical amplification resist where the photoacid generator is formulated into a resin component have been conventionally known and are used for several applications.

In such chemical amplification resist, the strong acid generated by the irradiation of the active energy ray acts as a catalyst to the resin component so as to change the solubility of the resin to the developing solution to form a pattern. For high sensitivity and high resolution, various resist materials have been developed, the combinations of the photoacid generators with the resins are limited. Therefore, the development of new chemical amplification resist is demanded.

The UV curing technology of a monomer and a prepolymer by the irradiation of active energy ray is classified roughly to three types of a radical type, a cationic type and an anionic type. Among them, the technique that vinyl monomers are polymerized by irradiation to photoradical polymerization initiator is the most widely developed. In addition, the technique that an acid generated by the action of light is used as cation to conduct cationic polymerization is also studied.

However, in the radical polymerization, because the polymerization is interrupted by the oxygen in the air, specific ingenuity is needed for blocking the oxygen. In the cationic polymerization, the block of the oxygen is not needed, which is more advantageous. However, the possible corrosivity and the resin modification caused by the strong acid generated from the photoacid generator remaining after curing are indicated. Therefore, it is strongly demanded that a photosensitive resin composition containing no corrosive material such as strong acid, being not inhibited by the oxygen in the air, and providing quick reaction progress in high efficiency is developed.

In view of the situations, the photosensitive resin composition containing an anionic photobase generator where the base generated by action of light is used for polymerization reactions and chemical reactions. However, the anionic photobase generator has a photosensitivity which is worse than the photosensitivity of a radical photopolymerization initiator and a cationic photoacid generator, therefore, strong activity energy ray is needed, which is disadvantageous for the anionic photobase generator.

Thus, a photobase generator capable of generating bases having high reactivity which is decomposed by irradiation is demanded. Furthermore, if an active species such as a radical in addition to a base is generated at the same time, the curing can proceed in higher efficiency.

Patent Literature 1 discloses a photosensitive resin composition containing a photoradical polymerization initiator, a photobase generator and an acrylate resin having an epoxy group. A radical and an amine occur from this photosensitive resin composition by the irradiation of the active energy ray, and the polymerization reaction of the acrylate group is induced by the radical at first, and then heating is conducted to provide the reaction of the amine and the epoxy group so as to produce the cured product.

However, the amine generated from an oxime photobase generator used in Patent Literature 1 is monofunctional, which does not work as a crosslinker for an epoxy resin. Therefore, there is a problem that in order to enhance the crosslink density of the cured product, a large amount of an acrylate having high cure shrinkage has to be added.

CITATION LIST

Patent Literature

Patent Literature 1: JP 2015-110765 A

Non Patent Literature

Non Patent Literature 1: J. Photopolym. Sci. Technol., Vol. 27, No 2 (2014), p 223-225

Non Patent Literature 2: Koji Arimitsu et al. KOBUNSHI RONBUNSHU (Japanese Journal of Polymer Science and Technology) Vol. 71, No. 2 (2014), p 53-58 (Feb. 25, 2014)

SUMMARY OF INVENTION

Technical Problem

The objects of the present invention are to provide a new compound capable of producing bases and radicals by the irradiation of the active energy ray, a photopolymerization initiator comprising the new compound and a photosensitive resin composition comprising the photopolymerization initiator, which has high sensitivity, and is excellent in storage stability and provides a cured product free from metal corrosion.

Solution to Problem

By the earnest research, the present inventors found to solve the problems by using a compound having a specific structure as an initiator so as to finish the present invention.

That is, the present invention relates to:

(1) A compound represented by the following formula (1):

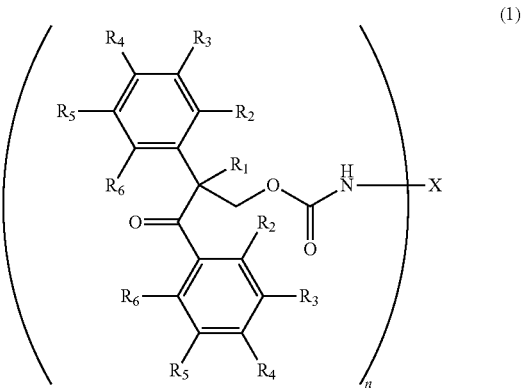

wherein in formula (1), $R_1$ represents a hydrogen atom, a hydroxyl group, an alkoxy group or an organic group other than the aforementioned substituents, when there are a plurality of $R_1$, each $R_1$ may be the same or different from each other; $R_2$ to $R_6$ each independently represent a hydrogen atom, a halogen atom, a hydroxyl group, an alkoxy group, mercapto group, a sulfide group, a silyl group, a silanol group, a nitro group, a nitroso group, a cyano group, a sulfino group, a sulfo group, a sulfonato group, a phosphino group, a phosphinyl group, a phosphono group, a phosphonato group, an amino group, an ammonio group or an organic group other than the aforementioned substituents; two or more selected from $R_2$ to $R_6$ on the same benzene ring may be connected to form a ring structure; X represents a residue being a saturated hydrocarbon including a ring structure from which n hydrogen atoms are removed; and n represents an integer of 1 to 6.

(2) The compound according to (1), represented by formula (2):

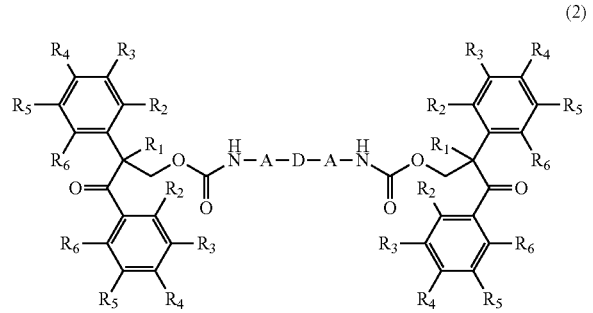

(2)

wherein in formula (2), $R_1$ to $R_6$ represent the same meanings as $R_1$ to $R_6$ in formula (1) described in (1); A represents a cycloalkylene group; and D represents an alkylene group.

(3) The compound according to (2), represented by formula (3):

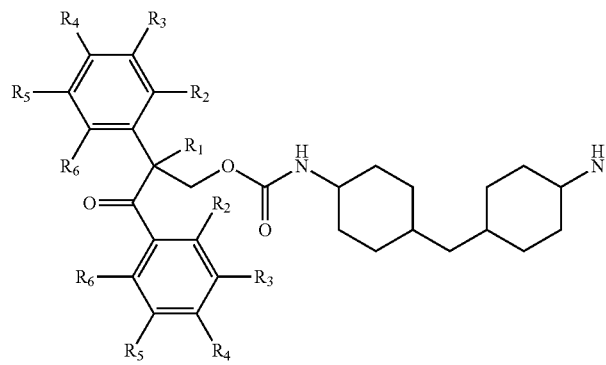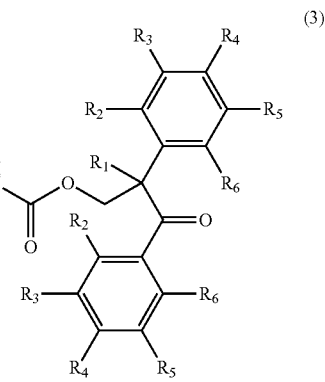

(3)

wherein in formula (3), $R_1$ to $R_6$ represent the same meanings as $R_1$ to $R_6$ in formula (2) described in (2).

(4) The compound according to any one of (1) to (3), wherein $R_1$ is a hydroxyl group.

(5) A photopolymerization initiator comprising the compound according to any one of (1) to (4).

(6) A photosensitive resin composition comprising a polymer precursor capable of being polymerized by irradiation or by both of irradiation and heating in the presence of a photopolymerization initiator, and the photopolymerization initiator according to (5).

(7) The photosensitive resin composition according to (6), wherein the polymer precursor comprises at least one selected from the group consisting of a compound having a substituent selected from the group consisting of an epoxy group, an isocyanate group, an oxetane group, an acryloyl group, a methacryloyl group, a maleimide group and a thiirane group; a polysiloxane precursor; a polyimide precursor; and a polybenzoxazole precursor.

(8) The photosensitive resin composition according to (7), wherein the polymer precursor comprises a compound having an epoxy group.

(9) A method for forming a pattern comprising the steps of:
changing solubility of an irradiation area by irradiation to a coat, a film or a formed body of the photosensitive resin composition according to any one of (6) to (8) in a predefined pattern, followed by heating or on heating; and
removing a non-irradiated area by performing development.

Effect of the Invention

The compound having the structure represented by formula (1) of the present invention is able to produce a base and a radical by the irradiation of the active energy ray. Because the produced base is a monofunctional or multifunctional amine having a high nucleophilic ring structure, which has high quantum yield of cleavage, the compound can be used as a photopolymerization initiator having the sensitivity superior to a conventional photobase generator. Furthermore, the photosensitive resin composition comprising the compound produces no acid providing metal corrosion by the irradiation of the active energy ray, therefore, the composition can be suitably used for metal materials.

FORM TO CARRY OUT INVENTION

Figure 1:
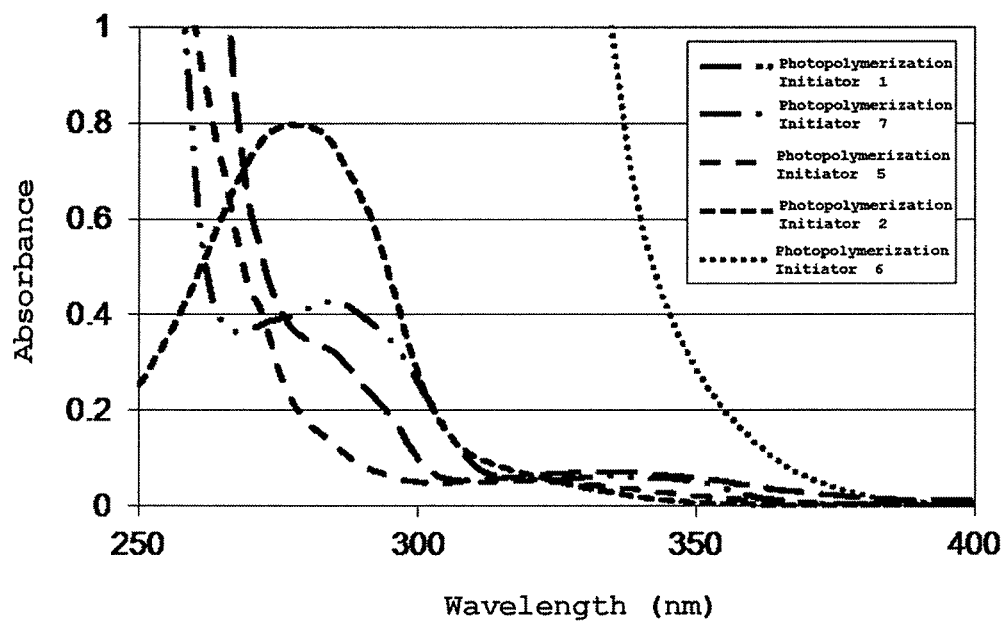
FIG. 1 shows the measurement results of the absorbances of the photopolymerization initiator of the present invention and the photopolymerization initiator for comparison.

The present invention is described below in detail. Note that the active energy ray in the present invention includes particle rays such as electron rays, and radical rays or ionization radiation which are generic terms of electromagnetic waves and particle rays in addition to visible light, provided that the case where a wavelength is specified is excluded. In this specification, the irradiation of the active energy ray may be referred to as exposure. Also, note that the active energy ray of a wavelength of 365 nm, 405 nm and 436 nm may be transcribed into i-ray, h-ray, and g-ray, respectively.

The compound of the present invention has a structure represented by formula (1).

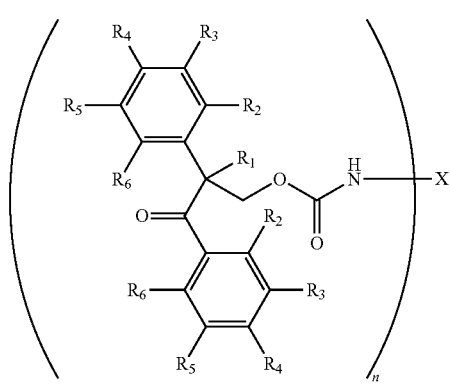

(1)

In formula (1), $R_1$ represents a hydrogen atom, a hydroxyl group, an alkoxy group or an organic group other than the aforementioned substituents, when there are a plurality of $R_1$, each $R_1$ may be the same or different from each other.

The alkoxy group represented by $R_1$ in formula (1) is preferably an alkoxy group having a carbon number of 1 to 18. Examples of the alkoxy group include a methoxy group, an ethoxy group, a n-propoxy group, an iso-propoxy group, a n-butoxy group, an iso-butoxy group, a sec-butoxy group, a t-butoxy group, a n-pentoxy group, an iso-pentoxy group, a neo-pentoxy group, a n-hexyloxy group and a n-dodecyloxy group.

Examples of "organic group other than the aforementioned substituents" represented by $R_1$ of formula (1) include an alkyl group having a carbon number of 1 to 18, an alkenyl groups having a carbon number of 2 to 18, an alkynyl group having a carbon number of 2 to 18, an aryl group having a carbon number of 6 to 12, an acyl group having a carbon number 1 to 18, an aroyl group having a carbon number of 7 to 18, a nitro group, a cyano group, an alkylthio group having a carbon number of 1 to 18 and a halogen atom.

Examples of the alkyl group having a carbon number of 1 to 18 described as the organic group represented by $R_1$ of formula (1) include a straight or branched alkyl group such as a methyl group, an ethyl group, a n-propyl group, an isopropyl group, a n-butyl group, an iso-butyl group, a sec-butyl, a t-butyl, a n-pentyl group, a n-hexyl group, a n-heptyl group, a n-octyl group, a n-nonyl group, a n-decyl, a n-undecyl group and a n-dodecyl group, and a cyclic alkyl group such as a cyclopropyl group, a cyclobutyl group, a cyclopentyl group and a cyclohexyl group. The alkyl group is preferably an alkyl group having a carbon number of 2 to 6, more preferably a linear or branched alkyl group having a carbon number of 2 to 6.

Examples of the alkenyl groups having a carbon number of 2 to 18 described as the organic group represented by $R_1$ of formula (1) include a vinyl group, a propenyl group, a 1-butenyl group, an iso-butenyl group, a 1-pentenyl group, a 2-pentenyl group, a 2-methyl-1-butenyl group, a 3-methyl-1-butenyl group, a 2-methyl-2-butenyl group, 2,2-dicyanovinyl group, a 2-cyano-2-methylcarboxyvinyl group and a 2-cyano-2-methylsulfonevinyl group.

Examples of the alkynyl group having a carbon number of 2 to 18 described as the organic group represented by $R_1$ of formula (1) include an ethynyl group, a 1-propynyl group and a 1-butynyl group.

Examples of the aryl groups having a carbon number of 6 to 12 described as the organic group represented by $R_1$ of formula (1) include a phenyl group, a naphthyl group and a tolyl group. The aryl group is preferably an aryl group having a carbon number of 6 to 10.

Examples of the acyl groups having a carbon number of 1 to 18 described as the organic group represented by $R_1$ of formula (1) include a formyl group, an acetyl group, an ethylcarbonyl group, a n-propylcarbonyl group, an iso-propylcarbonyl group, a n-butylcarbonyl group, a n-pentylcarbonyl group, an iso-pentylcarbonyl group, a neo-pentylcarbonyl group, a 2-methylbutyl carbonyl group and a nitrobenzylcarbonyl group.

Examples of the aroyl groups having a carbon number of 7 to 18 described as the organic group represented by $R_1$ of formula (1) include a benzoyl group, a toluoyl group, a naphthoyl group and a phthaloyl group.

Examples of the alkylthio group having a carbon number of 1 to 18 described as the organic group represented by $R_1$ of formula (1) include a methylthio group, an ethylthio group, a n-propylthio group, an iso-propylthio group, a n-butylthio group, an iso-butylthio group, a sec-butylthio group, a t-butylthio group, a n-pentylthio group, an iso-pentylthio group, 2-methylbutylthio group, a 1-methylbutylthio group, a neo-pentylthio group, a 1,2-dimethylpropylthio group and a 1,1-dimethylpropylthio group.

Examples of the halogen atom described of the organic group represented by $R_1$ of formula (1) include a fluorine atom, a chlorine atom, a bromine atom and an iodine atom.

$R_1$ in formula (1) is preferably an alkoxy group, more preferably an alkoxy group having a carbon number of 1 to 18, further preferably an alkoxy group having a carbon number of 1 to 6, especially preferably an alkoxy group having a carbon number of 1 to 4, and most preferably a methoxy group.

In formula (1), $R_2$ to $R_6$ each independently represent a hydrogen atom, a halogen atom, a hydroxyl group, an alkoxy group, a mercapto group, a sulfide group, a silyl group, a silanol group, a nitro group, a nitroso group, a cyano group, a sulfino group, a sulfo group, a sulfonate group, a phosphino group, a phosphinyl group, a phosphono group, a phosphonato group, an amino group, an ammonio group or an organic group other than the aforementioned groups. Also, two or more selected from $R_2$ to $R_6$ existing on the same benzene ring may be connected to form a ring structure, and the ring structure may contain a bond with a hetero atom.

Examples of the halogen atom represented by $R_2$ to $R_6$ of formula (1) includes the same one as the examples described in the halogen atoms represented by $R_1$ in formula (1).

Examples of the alkoxy group represented by $R_2$ to $R_6$ of formula (1) includes the same one as the examples described in the alkoxy group represented by $R_1$ in formula (1).

Examples of the organic group represented by $R_2$ to $R_6$ of formula (1) include an alkyl group, an aryl group, an aralkyl group, a halogenated alkyl group, an isocyano group, a cyanate group, an isocyanato group, a thiocyanato group, an isothiocyanato group, an alkoxycarbonyl group, a carbamoyl group, a thiocarbamoyl group, a carboxyl group, a carboxylate group, an acyl group, an acyloxy group, and a hydroxyimino group.

Examples of the alkyl group, the aryl group and the acyl group as examples of the organic group represented by $R_2$ and $R_6$ of formula (1) include the same one as the examples described in the alkyl group having a carbon number of 1 to 20, the aryl group having a carbon number of 6 to 20 and the acyl group having a carbon number of 1 to 20 represented by $R_1$ in formula (1).

These organic groups may include the bonds and the substituents with the hetero atoms in the organic group except for a hydrocarbon bonds, which may be linear or branched. The organic group of $R_2$ to $R_6$ is usually a monovalent organic group, but, in the cases where a ring structure is formed described below, the organic group may be a di- or more valent organic group.

In the organic group of $R_2$ to $R_6$, a bond except for the bonds of a hydrocarbon group can be included. The bond except for the bond of the hydrocarbon is not particularly limited as long as the advantageous effects are not damaged. Examples of the bond except for the bond of the hydrocarbon include an ether bond, a thioether bond, a carbonyl bond, a thiocarbonyl bond, an ester bond, an amide bond, a urethane bond, a carbonate bond, a sulfonyl bond, a sulfinyl bond, an azo bond. As a bond in the organic group except for the bond of the hydrocarbon group, in view of the heat resistant, an ether bond, a thioether bond, a carbonyl bond, a thiocarbonyl bond, an ester bond, an amide bond, a urethane bond, an imino bond (—N═C(—R)—, —C(═NR)— wherein R represents a hydrogen atom or an organic group), a carbonate bond, a sulfonyl bond and a sulfinyl bond are preferable.

The substituent except for the organic bond of $R_2$ to $R_6$ is not particularly limited as long as the advantageous effects are not damaged. The substituent except for the organic group includes a halogen atom, a hydroxyl group, a mercapto group, a sulfide group, a cyano group, an isocyano group, a cyanate group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxyl group, a carboxylate group, an acyl group, an acyloxy group, a sulfino group, a sulfo group, a sulfonato group, a phosphino group, a phosphinyl group, a phosphono group, a phosphonato group, a hydroxy imino group, a saturated or unsaturated alkyl ether group, a saturated or unsaturated alkylthio ether group, an aryl ether group and an arylthio ether group, an amino group (—NH₂, —NHR, and —NRR': wherein R and R' are independently a hydrocarbon group), and an ammonio group. The hydrogen included in the above substituents may be substituted by a hydrocarbon group. The hydrocarbon group included in the substituents may be linear, branched or cyclic. Among them, the preferable substituent except for the hydrocarbon group in the organic group of $R_2$ to $R_6$ is a halogen atom, a hydroxyl group, a mercapto group, a sulfide group, a cyano group, an isocyano group, a cyanato group, an isoxyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxyl group, a carboxylate group, an acyl group, an acyloxy group, a sulfino group, a sulfo group, a sulfonato group, a phosphino group, a phosphinyl group, a phosphono group, a phosphonato group, a hydroxyimino group, a saturated or unsaturated alkyl ether group, a saturated or unsaturated alkylthioether group, an arylether group and an arylthioether group.

Also, two or more of $R_2$ to $R_6$ may be bonded to each other to form a cyclic structure.

The cyclic structure may be a saturated or unsaturated alicyclic hydrocarbon, a heterocyclic hydrocarbon, a condensed ring hydrocarbon and a structure having the combination of two or more selected from the saturated or unsaturated alicyclic hydrocarbon, the heterocyclic hydrocarbon and the condensed ring hydrocarbon. For example, two or more of $R_2$ to $R_6$ are bonded to each other to share the atoms of the benzene ring bonded to $R_2$ to $R_6$ so as to form a condensed ring such as a naphthalene, an anthracene, a phenanthrene and an indene.

In the present invention, one or more of substituents are preferably introduced into $R_2$ to $R_6$. That is, at least one of $R_2$ to $R_6$ may have, as a substituent, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group or an organic group other than the aforementioned substituents. By introduction of at least one of such substituents described above into substituents $R_2$ to $R_6$, the wavelength of absorbed light may be controlled. Also, light having a desired wavelength may be absorbed by introduction of the substituent. Furthermore, the substituent that extends the conjugated chain of the aromatic ring may be introduced to shift the absorbed wavelength to a longer wavelength. In particular, when the mercapto group and the sulfide group including the sulfur atom are introduced into substituents $R_2$ to $R_6$, the absorbance region may largely shift to a longer wavelength. Furthermore, the solubility and the compatibility to a polymer precursor with which the compound is combined may be improved. Thereby, the sensitivity of the photosensitive resin composition may be improved, while the absorbed wavelength of the polymer precursor combined is considered.

The preferred examples of the organic group of $R_2$ to $R_6$ an alkyl group having a carbon number of carbon 1 to 20 such as a methyl group, an ethyl group and a propyl group; a cycloalkyl group having a carbon number of 4 to 23 such as a cyclopentyl group and a cyclohexyl group; a cycloalkenyl group having a carbon number of 4 to 23 such as a cyclopentenyl group and a cyclohexenyl group; an aryloxy alkyl group (—ROAr group) having a carbon number of 7 to 26 such as a phenoxymethyl group, a 2-phenoxyethyl group, a 4-phenoxybutyl group; an aralkyl group having a carbon number of 7 to 20 such as a benzyl group, a 3-phenylpropyl group; an alkyl group having a cyano group having a carbon number of 2 to 21 such as a cyanomethyl group and a R-cyanoethyl group; an alkyl group having a hydroxyl group having a carbon number of 1 to 20 such as a hydroxylmethyl group; an alkoxy group having a carbon number of 1 to 20 such as a methoxy group and an ethoxy group; an amido group having a carbon number of 2 to 21 such as an acetamide group and a benzenesulfonamide group ($C_6H_5SO_2NH_2$—); an alkylthio group (—SR group) having a carbon number of 1 to 20 such as a methylthio group and an ethylthio group; an acyl group having a carbon number of 1 to 20 such as an acetyl group and a benzoyl group; an ester group (—COOR group and —OCOR group) having a carbon number of 2 to 21 such as a methoxy carbonyl group and an acetoxy group; an aryl group having a carbon number of 6 to 20 such as a phenyl group, a naphthyl group, a biphenyl group and a tolyl group; an aryl group having a carbon number of 6 to 20 where an electron-donating group and/or an electron-withdrawing group is/are substituted; a benzyl group where an electron-donating group and/or an electron-withdrawing group is/are substituted; a cyano group; and a methylthio group (—SCH₃ group). The alkyl moiety of the substituent described above may be linear, branched or cyclic.

Also, two or more of $R_2$ to $R_6$ may be bonded to each other to share the atoms of the benzene ring bonded to $R_2$ to $R_6$ so as to form a condensed ring such as a naphthalene, an anthracene, a phenanthrene, and an indene, which are preferable in view of shifting the absorbed wavelength to a longer wavelength.

In the photopolymerization initiator of the present invention, it is preferred that at least one of $R_2$ to $R_6$ is a hydroxyl group in view of improving the solubility and making the absorbed wavelength longer, compared with a case where none of $R_2$ to $R_6$ is a hydroxyl group.

It is preferable that all of $R_2$ to $R_6$ in formula (1) are hydrogen atoms, or that $R_2$, $R_3$, $R_5$ and $R_6$ are hydrogen atoms, and $R_4$ is an alkoxy group.

In formula (1), X represents a residue of a saturated hydrocarbon having a ring structure from which n hydrogen atoms (n means number) are removed (hereinafter, in some cases, simply mentioned as a "saturated hydrocarbon residue" in the specification). Examples of the ring structure included in the saturated hydrocarbon residue include a saturated hydrocarbon having a three to ten-membered ring, and the saturated hydrocarbon residue may have one or more ring structures. Specifically, examples of the ring structure included in the saturated hydrocarbon residue include a structure such as a cyclopropane ring, a cyclobutane ring, a cyclopentane ring, a cyclohexane ring and an adamantane ring.

the same meanings as preferred $R_1$ to $R_6$ in formula (1). A represents a cycloalkylene group. D represents an alkylene group.

The cycloalkylene group represented by A in formula (2) is a divalent linking group of a saturated cyclic hydrocarbon from which two hydrogen atoms are removed, and examples of the saturated cyclic hydrocarbon include a cyclopropane ring, a cyclobutane ring, a cyclopentane ring, a cyclohexane ring and an adamantane ring. The linking group is preferably a 1,3-cyclopentylene group and a 1,4-cyclohexylene group, more preferably 1,4-cyclohexylene group.

The alkylene groups represented by D in formula (2) is a divalent linking group of a saturated aliphatic hydrocarbon (e.g., methane, ethane, propane, butane, pentane, hexane, heptane and octane) from which two hydrogen atoms are removed. The divalent linking group is preferably an alkylene group having a carbon number 1 to 18, more preferably an alkylene group having a carbon number of 1 to 12, further preferably a linear alkylene group having a carbon number of 1 to 8 (specifically, a methylene group, an ethylene group, a propylene group, a butylene group, a pentylene group, a hexylene group, a heptylene group, and an octylene group), particularly preferably an alkylene group having a carbon number of 1 to 4, and the most preferably an alkylene group having a carbon number of 1, that is a methylene.

Namely, the compound represented by formula (2) is preferably a compound represented by formula (3).

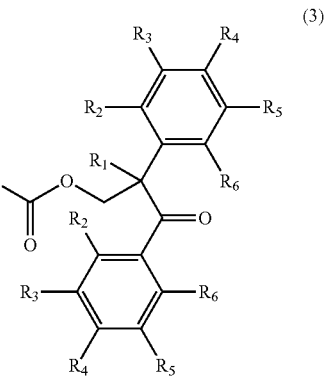

(3)

In formula (1), n represents an integer of 1 to 6, preferably 1 to 2, more preferably 2. That is, the compound represented by formula (1) of the present invention is preferably a compound represented by formula (2)

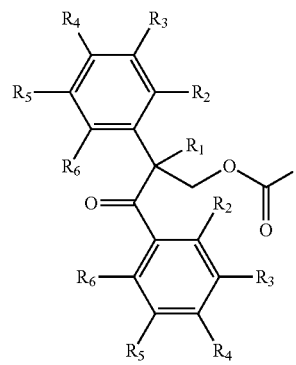

(2)

In formula (2), $R_1$ to $R_6$ represent the same meanings as $R_1$ to $R_6$ in formula (1), and the preferred $R_1$ to $R_6$ are also In formula (3), $R_1$ to $R_6$ represent the same meanings as $R_1$ to $R_6$ in formula (2), and the preferred $R_1$ to $R_6$ in formula (3) are also the same meanings as the preferred $R_1$ to $R_6$ in formula (1).

The compound represented by formula (1) of the present invention generates a radical and a basic compound in connection with a cleavage reaction and a decarboxylation reaction as shown in the reaction described below by the irradiation of active energy ray so as to start a radical polymerization of a polymer precursor having a radical polymerizable group. The basic compound which is generated at the same time of radical not only may conduct a cross-linking reaction with a polymer precursor described below, but also may lower the curing starting temperature of the polymer precursor by the catalytic action of the generated base.

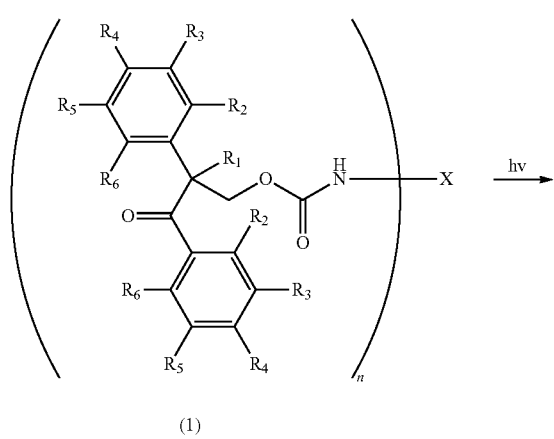

(1)

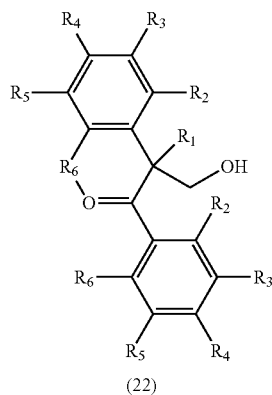

(22)

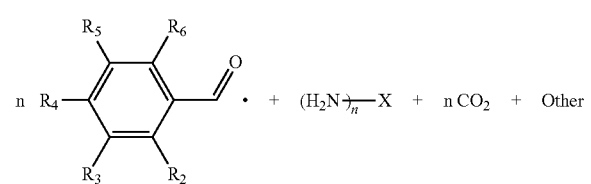

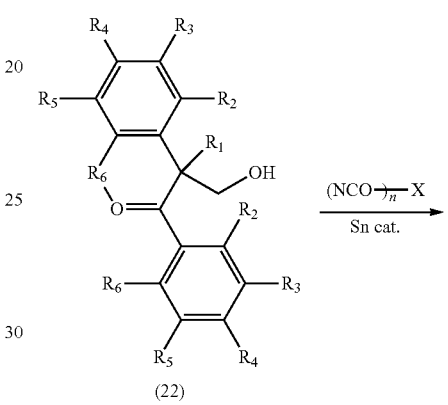

(22)

Next, the synthetic method of the compound represented by formula (1) of the present invention will be explained.

The compound represented by formula (1) of the present invention can be synthesized by the application of the well-known method. By the application of a method disclosed in J. Photopolym. Sci. Technol 27, 2, various compounds can be synthesized. For example, a paraformaldehyde is reacted with a benzoin derivative represented by formula (22) in the presence of a metal hydroxide at a room temperature for 30 minutes to produce an intermediate compound. After that, the intermediate compound is reacted with an isocyanate in the presence of an organic compound including tin or lead, etc., so as to obtain the compound represented by formula (1). However, the synthesis method of the compound represented by formula (1) is not limited to the above method. As a purified method for the compound having high crystalline nature, a crystallization method is suitable. Alternatively, purification may be conducted by washing using a solvent. Note that X, $R_1$ to $R_6$ and n in formulas (21) and (22) represent the same meanings as X, $R_1$ to $R_6$ and n in formula (1).

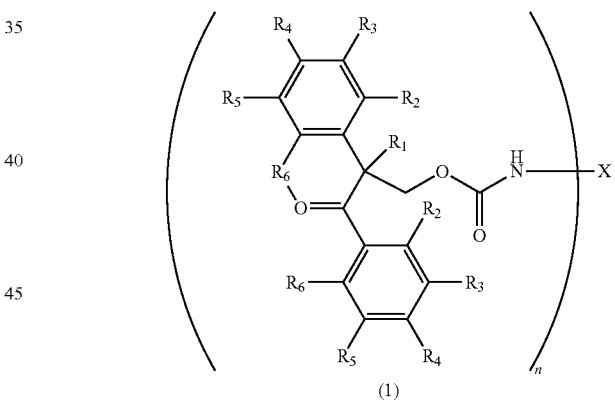

(1)

Specifically, examples of the compound represented by formula (1) are shown as formulas (a) to (h) described below, but the present invention is not limited to these compounds.

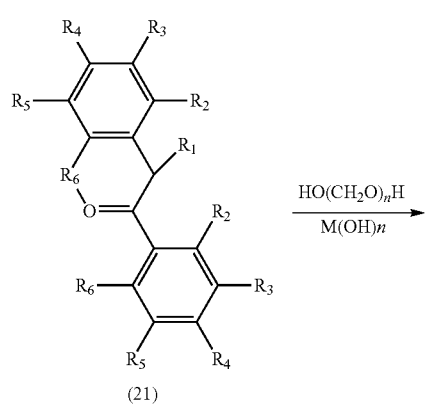

(21)

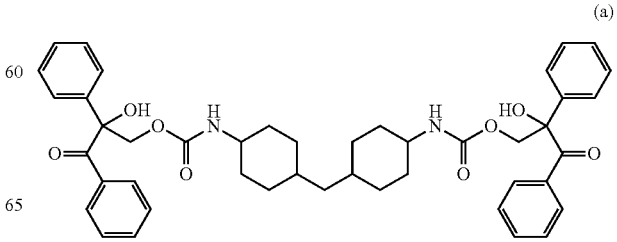

(a)

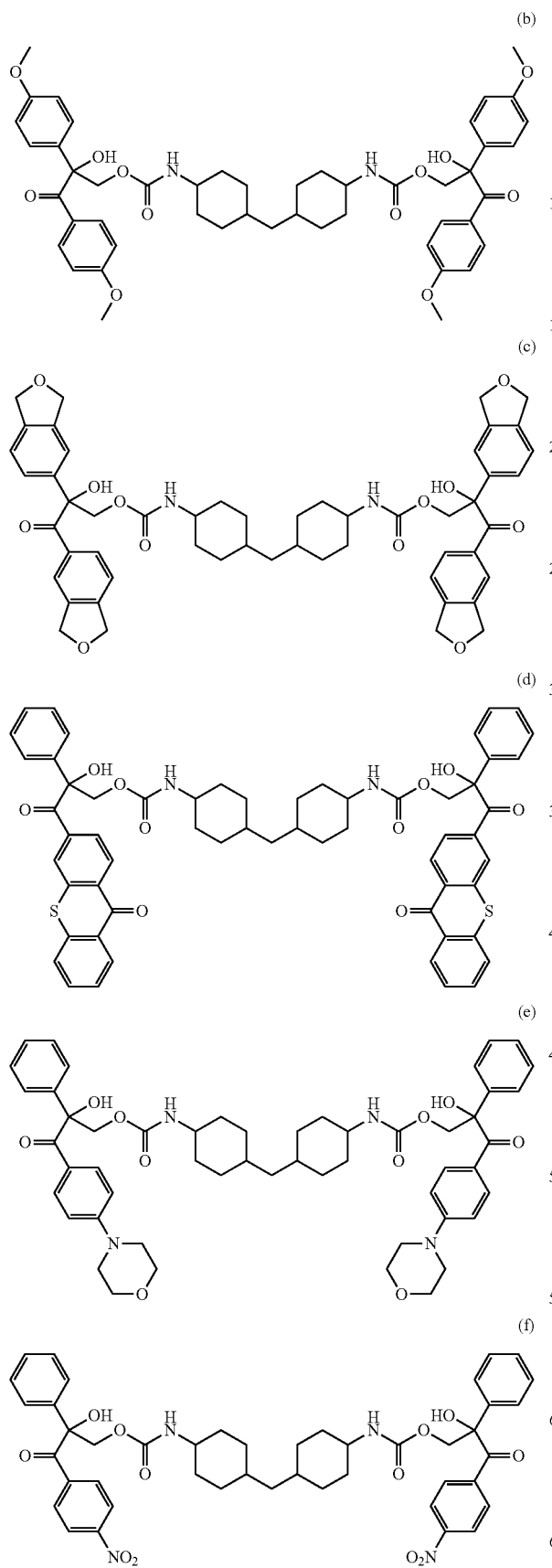

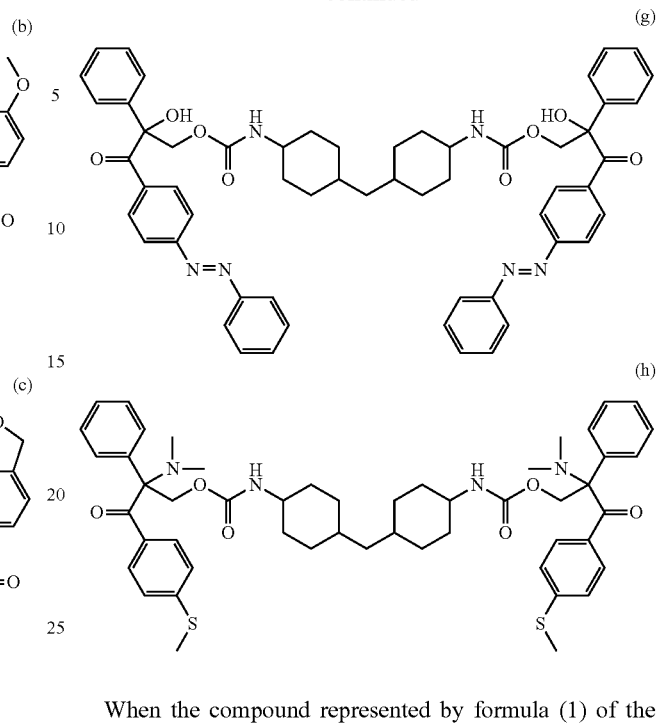

When the compound represented by formula (1) of the present invention is used as a photopolymerization initiator, the compound needs to have the absorption in at least part of the exposure wavelength to produce a radical and a basic compound which can contribute sufficiently to the polymerization reaction or the condensed polymerization reaction of the polymer precursor. Because the wavelength of the high-pressure mercury vapor lamp which is a general exposure light source is 365 nm, 405 nm and 436 nm, the compound preferably has the absorption in a region including at least one of these wavelengths of the activity energy ray. The cases are preferable in view of further increasing the kinds of applicable polymer precursors.

When the compound represented by formula (1) is used as a photopolymerization initiator, the molar absorbance coefficient is preferably 100 or more to the active energy ray having a wavelength of 365 nm, or 1 or more to the active energy ray having a wavelength of 405 nm in view of further increasing the kinds of applicable polymer precursors.

The absorbance at the wavelength region described above which the compound represented by formula (1) has can be confirmed by solving the compound in a solvent (e.g., acetonitrile) which has no absorbance in the wavelength region to make a concentration of not more than $1\times10^{-4}$ mol/L (usually about from $1\times10^{-4}$ mol/L to $1\times10^{-5}$ mol/L) of the base generator represented by formula (1) and measuring the absorbance of the solution by a ultraviolet and visible spectrophotometer (for example, UV-2550 manufactured by Shimazu Corporation).

The photopolymerization initiator (photobase generator) including the compound represented by formula (1) of the present invention has various applicability because of having sensitivity superior to a conventional photobase generator. The compound may be combined with not only a polymer precursor described below which is capable of being (condensation) polymerized by a base material or by heating in the presence of a base material, but also a compound capable of changing the structure or the properties thereof by a base such as an acid-base indicator, etc., so as to obtain the photosensitive composition.

Such photosensitive compositions may be used for a paint, a printing ink, a sealant, an adhesive, a display device, a semiconductor device, an electronic part, a micro electro mechanical system (MEMS), an optical material or an architectural material.

For example, an image formation media capable of being obtained by covering or impregnating a substrate with an image formation layer including photopolymerization initiator (photobase generator) including the compound represented by formula (1) of the present invention and the acid-base indicator may be applied to a display device, such as an image formation media comprising a display formation layer to be exposed to produce a base from the photobase generator, which may be reacted with an acid-base indicator so as to form an image.

<Photosensitive Resin Composition>

The photosensitive resin composition of the present invention contains a polymer precursor which can be polymerized by irradiation or by irradiation and heating in the presence of the photopolymerization initiator including the compound represented by formula (1). The pattern using the photosensitivity resin of the present invention can be formed by making the difference of the solubility of exposed areas and unexposed areas, namely, by increasing the contrast of solubility due to change of the solubility through the polymerization of the polymer precursor.

<Polymer Precursor>

The polymer precursor contained in the photosensitive resin composition of present invention means a compound capable of becoming a cured product by increasing the molecular weight by the polymerization caused by a radical or a base material or by heating in the presence of a base material. Examples of the polymerization aforementioned above include polymerization between the polymer precursors caused by a radical and condensation polymerization between a polymer precursor and a base compound (e.g. amines) generated from the compound represented by formula (1). In addition to those, the embodiments of the photosensitive resin composition of the present invention also include a case that the base compound generated from the compound represented by formula (1) works as a catalyst to lower the reaction start temperature of heat curing. The molecular weight of the polymer precursor is not limited to, but preferably about 500 to 10,000 of a weight (or a number) average molecular weight.

The polymer precursor contained in the photosensitive resin composition of present invention is not particularly limited, as long as the polymer precursor is a compound capable of increasing a molecular weight by polymerization caused by a radical generated from the compound represented by formula (1), a compound capable of (condensation) polymerization by a base material generated from the compound represented by a formula (1) or by heating in the presence of a base material, and a compound capable of lowering the reaction start temperature of (condensation) polymerization by act as a catalyst of a base material. Examples of the polymer precursor are described below, but the polymer precursor contained in the photosensitive resin composition of the present invention is not limited to these.

<Polymer Precursor Providing Polymer by Radical Polymerization>

Examples of the polymer precursor capable of increasing molecular weight by polymerization caused by a radical generated from the compound represented by formula (1) include a compound having a substituent having radical polymerization properties. The compound having one or more substituents having radical polymerization properties is preferably a compound having a double bond in the molecule thereof, and is preferably a compound having an allyl group, an acryloyl group, a methacryloyl group or a maleimide group.

Specifically, examples of the compound having an acryloyl group or a methacryloyl group (provided that a compound having an epoxy group is excluded) include a diacrylate of diol such as 1,4-butanediol diacrylate, 1,6-hexanediol diacrylate, 1,9-nonanediol diacrylate and 1,10-decanediol diacrylate, a diacrylate of glycol such as ethyleneglycol diacrylate, diethyleneglycol diacrylate, triethyleneglycol diacrylate, tetraethyleneglycol diacrylate, polyethyleneglycol diacrylate, dipropyleneglycol diacrylate, tripropylene glycol diacrylate, polypropyleneglycol diacrylate, neo-pentyl glycol diacrylate, diacrylate of a diol obtained by adding at least one of ethylene oxide and propylene oxide to neopentylglycol and caprolactone modification hydroxypivalic acid neopentylglycol diacrylate; a diacrylate having a ring structure such as a diacrylate of EO adduct of bisphenol A, a diacrylate of PO adduct of bisphenol A, tricyclodecandimethanol diacrylate, hydrogenated dicyclopentadienyl diacrylate and cyclohexyl diacrylate.

Specifically, examples of the commercial products of the compound having an acryloyl group or a methacryloyl group include LIGHTACRYLATE 1, 6HX-A, 1,9ND-A, 3EG-A and 4EG-A (all are product names, manufactured in Kyoeisha chemical Co., Ltd.); HDDA, 1,9-NDA, DPGDA and TPGDA (all are product names, manufactured by Daicel-Allnex LTD.), BSCOAT #195, #230, #230D, #260, #310HP, #335HP and #700HV (all are product names, manufactured by OSAKA ORGANIC CHEMICAL INDUSTRY LTD.), ALLONICS M-208, M-211B, M-220, M-225, M-240, M-270 (all are product names, manufactured by Toagosei Company, Limited.).

Among them, from the viewpoint of the viscosity and the compatibility with the compound represented by formula (1), a diacrylate having an alkyl chain of carbon number of 4-12, particularly, 1,4-butanediol diacrylate, 1,6-hexanediol diacrylate, 1,9-nonanediol diacrylate or 1,10-decanediol diacrylate is preferred.

<Polymer Precursor Providing Polymer by Intermolecular Reaction>

Examples of a polymer precursor capable of increasing molecular weight by intermolecular reaction by a base material generated from the compound represented by formula (1) or by heating in the presence of the base material include a compound having a substitute capable of reacting with the base material or a compound capable of increasing molecular weight by reaction (cross-linking reaction) for forming a bond between molecules in the presence of the base material. Examples of the substituent capable of reacting with the base material and the substituent capable of reaction for forming a bond between molecules by heating in the presence of the base material include an epoxy group, an oxetane group, a thiirane group, an isocyanate group, a hydroxyl group, and a silanol group. In the polymer precursor, a compound capable of performing hydrolysis and polycondensation is included. Examples of the substituent capable of performing hydrolysis and polycondensation between molecules include —SiX of a polysiloxane precursor wherein the X is a hydrolysable group selected from the group consisting of an alkoxy group, an acetoxy group, an oxime group, an enoxy group, an amino group, an aminoxy group, an amide group and a halogen.

Examples of the compound having a substituent capable of reacting with a base material include a compound having at least one substituents mentioned above, for example, a compound having one or more of epoxy groups in the molecule, a compound having one or more oxetane groups in the molecule, a compound having one or more thiirane groups in the molecule.

The compound having an epoxy group is specifically explained below, but a compound having an oxetane group or a thiirane group can be used in the same manner.

<Compound Having Epoxy Group>

The compound having an epoxy group is not particular limited and the conventional one can be used, as long as the compound has one or more epoxy groups.

Also, the photoinitiator containing the compound represented by formula (1) of the present invention usually works as a curing catalyst for the compound having one or more epoxy groups in the molecular.

When the compound having one or more epoxy groups in the molecule is used, a compound having two or more functional groups having the reactivity with the epoxy group may be used together. Examples of the functional group having the reactivity with the epoxy group include a carboxyl group, a phenolic hydroxyl group, a mercapto group, and a primary or a secondary aromatic amino group. The compound having two or more functional groups having the reactivity with the epoxy group in the molecule include a compound having a weight average molecular weight of 3,000 to 100,000 wherein the functional group is introduced into the polymer side chain. The embodiment where this compound is used together is one of the preferred embodiments. When the weight average molecular weight of the polymer is less than 3,000, the strength of the film decreases, and tuck (sticky) occurs on the surface of the cured film resulting in easy adherence of impurity to the cured film. When the weight average molecular weight of the polymer is more than 100,000, the viscosity at the time of solving the polymer in a solvent or the melt viscosity may increase.

Examples of the compound having one or more epoxy group in the molecule include a bisphenol A-type epoxy resin derived from a bisphenol A and an epichlorohydrin, a bisphenol F-type epoxy resin derived from a bisphenol F and an epichlorohydrin, a bisphenol S-type epoxy resin, a phenol novolac-type epoxy resin, a cresol novolac-type epoxy resin, a bisphenol A novolac-type epoxy resin, a bisphenol F novolac-type epoxy resin, an alicyclic-type epoxy resin, a diphenyl ether-type epoxy resin, a hydroquinone-type epoxy resin, a naphthalene-type epoxy resin, a biphenyl-type epoxy resin, a fluorene-type epoxy resin, a multifunctional-type epoxy resin such as trifunctional-type epoxy resin or tetrafunctional-type epoxy resin, a glycidyl ester-type epoxy resin, a glycidylamine-type epoxy resin, a hydantoin-type epoxy resin, an isocyanurate-type epoxy resin, and an aliphatic chain epoxy resin. These epoxy resins may be halogenated or hydrogenated. Examples of the epoxy resin which is commercially available include jER COAT 828, 1001, 801N, 806, 807, 152, 604, 630, 871, YX8000, YX8034, YX4000 (all are manufactured by JAPAN EPOXY RESIN LTD.), EPICLON 830, EXA835LV, HP4032D, HP820 (all are manufactured by DIC Corporation), EP4100 series, EP4000 series, EPU series (all are manufactured by ADEKA Co., Ltd.), CELLOXYIDE series (2021, 2021P, 2083, 2085, and 3000, etc.) EPOLEAD series and EHPE series, (all are manufactured by DICEL Corporation), YD series, YDF series, YDCN series and YDB series (all are manufactured by Tohto kasei Co., Ltd.), DENACOL series (manufactured by NAGASE Chemtex Corporaton), Epolite series (manufactured by Kyoei chemical Co., Ltd), but the compound is not particularly limited to these. Two or more of these epoxy resins may be used together. Not only because several grades having different molecular weights are widely available, but also because adhesive properties or reactivity may be optionally selected, the bisphenol-type epoxy resin is preferred.

<Compound Having Oxetane Group>

Examples of the compound having an oxetane group include multi-functional oxetane compounds such as difunctional oxetane compound such as 4,4'-(3-ethyloxetane-3-yl-methyloxymethyl)biphenyl (OXBP), 3-ethyl-3-hydroxymethyloxetane (EHO), 1,4-bis[{(3-ethyl-3-oxetanyl)methoxy}methyl]benzene (XDO), di[l-ethyl(3-oxetanyl)]methylether (DOX), di[l-ethyl (3-oxetanyl)]methylether (DOE), 1,6-bis[(3-ethyl-3-oxetanyl)methoxy]hexane (HDB), 9,9-bis[2-methyl-4-{2-(3-oxetanyl)}butoxy phenyl]fluorene, 9,9-bis[4-[2-{2-(3-oxetanyl)}butoxy]ethoxyphenyl]fluorene, and an oxetanated novolac resin.

<Compound Having Thiirane Group>

The compound having a thiirane group is a compound having one or more thiirane group in the molecule, for example, bis(2,3-epithiopropyl)sulfide, bis(2,3-epithiopropylthio)ethane, bis(2,3-epithiopropylthio)propane, bis(2,3-epithiopropylthio)butane, bis(5,6-epithio-3-thiohexane)sulfide, bis(2,3-epithiopropyl)disulfide, bis(3,4-epithiobutyl)disulfide, bis(4,5-epithiopentyl)disulfide and bis(5,6-epithiohexyl)disulfide. Bis(2,3-epithiorpropyl)sulfide and bis(2,3-epithiopropyl)disulfide are particularly preferred.

Examples of the compound performing cross-linking reaction between molecules include a combination of a compound having two or more isocyanate groups in the molecule with a compound having two or more hydroxy groups in the molecule. By reaction of the isocyanate groups with the hydroxy groups, a urethane bond between the molecules are formed to make a polymer.

<Compound Having Isocyanate Group>

The compound having an isocyanate group is not particularly limited as long as the compound has two or more isocyanates groups in the molecule. The conventional one can be used. Examples of such compounds include low molecular weight compounds represented by p-phenylene diisocyanate, 2,4-toluene diisocyanate, 2,6-toluene diisocyanate, 1,5-naphthalene diisocyanate, hexamethylene diisocyanate as well as an oligomer and a compound having a weight average molecular weight of 3,000 or more, of which the side chain or the terminal part has an isocyanate group.

<Compound Having Hydroxyl Group>

The compound having an isocyanate group are usually used in combination with a compound having a hydroxyl group in the molecule. The compound having a hydroxy group is not particularly limited, as long as the compound has two or more hydroxyl groups in the molecule. Examples of such compounds include a small molecular weight compound such as ethylene glycol, propylene glycol, glycerin, diglycerine and pentaerythritol, as well as a compound of which the side chain or the terminal part has a hydroxy group, which is a compound has a weight average molecular weight of 3,000 or more.

<Polysiloxane Precursor>

Examples of the compound performing hydrolysis and polycondensation between the molecules also include a polysiloxane precursor. Examples of the polysiloxane precursor include an organic silicon compound represented by $Y_nSiX_{(4-n)}$ (wherein, Y represents an alkyl group, a fluoroalkyl group, a vinyl or a phenyl group which may have substituent or hydrogen, and X represents a hydrolysable group selected from the group consisting of an alkoxy group, an acetoxy group, an oxime group, an enoxy group, an amino group, an aminoxy group, an amido group and a halogen atom. n shows an integer of 0 to 3) and the hydrolysis polycondensation products of the organic silicon compound. In formula $Y_nSiX_{(4-n)}$, n is preferably 0 to 2. From a viewpoint of easily preparing a silica dispersion oligomer solution and easy availability, the hydrolysable group is preferably an alkoxy group. The organic silicon compound mentioned above is not particularly limited, and the conventional one can be used. Examples of the organic silicon compound include trimethoxysilane, triethoxysilane, methyltrichlorosilane, methyltrimethoxysilane, methyltriethoxysilane, methyltriisopropoxysilane, methyltri-t-butoxysilane, ethyltribromosilane, ethyltrimethoxysilane, ethyltriethoxysilane, n-propyltriethoxysilane, n-hexyltrimethoxysilane, phenyltrimethoxysilane, phenyltriethoxysilane, tetramethoxysilane, tetraethoxysilane, tetrabutoxysilane, dimethoxydiethoxysilane, dimethyldichlorosilane, dimethyldimethoxysilane, diphenyldimethoxysilane, vinyltrimethoxysilane, trifluoropropyltrimethoxysilane, γ-glycidoxypropylmethyldiethoxysilane, γ-glycidoxypropyltrimethoxysilane, γ-methacryloxypropylmethyldimethoxysilane, γ-aminopropylmethyldimethoxysilane, γ-mercaptopropylmethyldiethoxysilane, γ-mercaptopropyltrimethoxysilane, β-(3,4-epoxycyclohexyl)ethyltrimethoxysilane, fluoroalkylsilane known as a fluorine silane coupling agent and the hydrolysis condensates or the cohydrolysis condensates thereof, and the mixtures thereof.

<Polymer Precursor Providing Polymer by Ring Closure Reaction in Molecule>

Examples of the polymer precursor capable of increasing the molecular weight by the ring closure reaction in the molecule include a polyimide precursor, a polybenzoxazole precursor. These precursors may be a mixture of two or more polymer precursor.

The polyimide precursor and the polybenzoxazole precursor which are the preferable polymer precursor of the present invention are explained below, but the present invention is not particularly limited.

<Polyimide Precursor>

For a polyimide precursor, a polyamick acid having a repeating unit represented by the following formula (8) is preferably used. In formula (8), $R_7$ is a tetravalent organic group. $R_8$ is a divalent organic group. $R_9$ and $R_{10}$ are a hydrogen atom or an organic group. n is natural number of 1 or more. For example, when $R_9$ and $R_{10}$ are an organic group, examples of the organic group of $R_9$ and $R_{10}$ include an alkyl group, an alkenyl group, an alkynyl group, an aryl group and a structure which is the group mentioned above including an ether bond, represented by $C_nH_{2n}OC_mH_{2m+1}$.

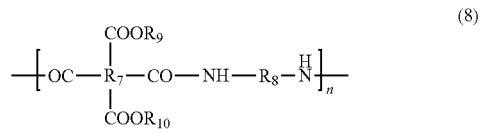

(8)

A polyamick acid is preferred, because the polyamick acid can be synthesized just by mixing a dianhydride with a diamine in a solution, that is, through one step reaction, and further can be obtained in simple synthesis at a low cost.

When the polymer precursor is a polyamick acid having a repeating unit represented by formula (8), the temperature required for imidization can be lowered to usually less than 300° C., preferably 250° C. or less due to the catalyst effects of the base material. Note that when the general polyamic acid is used, the temperature required for imidization is 300° C. or more. Therefore, the application of the products using the general polyamic acid is limited. However, because the temperature required for imidization can be lowered, the products can be applied to more various applications.

For a method for manufacturing a polyimide precursor, the conventional technique can be used. Examples of the method include a method for synthesizing the polyamide acid which is a precursor from a dianhydride and a diamine, a method where a diamino compound or the derivative thereof is reacted with an ester acid or a carboxylic acid of an amide acid monomer obtained by reacting a dianhydride with a monohydric alcohol, an amino compound, or an epoxy compound, etc., but the method is not limited to these examples.

<Polybenzoxazole Precursor>

For a polybenzoxazole precursor, a polyamide alcohol having a repeating unit represented by the following formula (9) is preferably used.

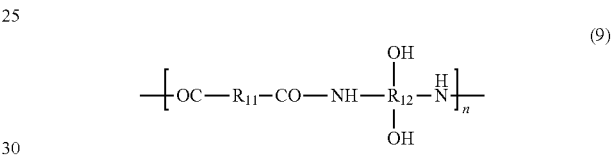

(9)

In formula (9), $R_{11}$ is a divalent organic group, and $R_{12}$ is a tetravalent organic group. The polyamide alcohol having a repeating unit represented by formula (9) may contain a single repeating unit or two or more repeating units.

Examples of a dicarboxylic acid and the derivatives thereof which are applicable to the reaction for obtaining the polybenzoxazole precursor mentioned above include phthalic acid, isophthalic acid, terephthalic acid, 4,4'-benzophenonedicarboxylic acid, 3,4'-benzophenonedicarboxylic acid, 3,3'-benzophenonedicarboxylic acid, 4,4'-biphenyldicarboxylic acid, 3,4'-biphenyldicarboxylic acid, 3,3'-biphenyldicarboxylic acid, 4,4'-diphenyletherdicarboxylic acid, 3,4'-diphenyletherdicarboxylic acid, 3,3'-diphenyletherdicarboxylic acid, 4,4'-diphenylsulfonedicarboxylic acid, 3,4'-diphenylsulfonedicarboxylic acid, 3,3'-diphenylsulfonedicarboxylic acid, 4,4'-hexafluoroisopropylidenedibenzoic acid, 4,4'-dicarboxy diphenylamide, 1,4-phenylenediethanoic acid, 1,1-bis(4-carboxyphenyl)-1-phenyl-2,2,2-trifluoroethane, bis(4-carboxyphenyl)tetraphenyldisiloxane, bis(4-carboxy phenyl)tetramethyldisiloxane, bis(4-carboxyphenyl)sulfone, bis(4-carboxy phenyl)methane, 5-t-butylisophthalic acid, 5-bromoisophthalic acid, 5-fluoroisophthalic acid, 5-chloroisophthalic acid, 2,2-bis-(p-carboxy phenyl)propane, 4,4'-(p-phenylenedioxy)dibenzoic acid, 2,6-naphthalenedicarboxylic acid or an acid halide thereof and an active ester thereof with a hydroxydibenzotriazole, but the polybenzoxazole precursor is not limited to these examples. These are used alone or in combination of two or more.

Specifically, examples of a hydroxydiamine which is applicable to reaction for obtaining the polybenzoxazole precursor include 3,3'-dihydroxybenzidine, 3,3'-diamino-4,4'-dihydroxybiphenyl, 4,4'-diamino-3,3'-dihydroxybiphenyl, 3,3'-diamino-4,4'-dihydroxydiphenylsulfone, 4,4'-diamino-3,3'-dihydroxydiphenylsulfone, bis-(3-amino-4-hydroxyphenyl)methane, 2,2-bis-(3-amino-4- hydroxyphenyl)propane, 2,2-bis-(3-amino-4-hydroxyphenyl)hexafluoropropane, 2,2-bis-(4-amino-3-hydroxyphenyl)hexafluoropropane, bis-(4-amino-3-hydroxyphenyl)methane, 2,2-bis-(4-amino-3-hydroxyphenyl)propane, 4,4'-diamino-3,3'-dihydroxybenzophenone, 3,3'-diamino-4,4'-dihydroxybenzophenone, 4,4'-diamino-3,3'-dihydroxydiphenylether, 3,3'-diamino-4,4'-dihydroxydiphenylether, 1,4-diamino-2,5-dihydroxybenzene, 1,3-diamino-2,4-dihydroxybenzene, 3-diamino-4,6-dihydroxybenzen, but the hydroxydiamine is not particularly limited. These compounds are used alone or in combination of two or more.

In order to increase the sensitivity and to obtain a pattern form which accurately reproduces a mask pattern when made into the photosensitivity resin composition, the transmittance of the polymer precursor such as the polyimide precursor or the polybenzoxazole precursor, etc., is preferably 5% or more, more preferably 15% or more to the exposure wavelength at the thickness of 1 μm. High transmittance of the polymer precursor such as the polyimide precursor or the polybenzoxazole precursor, etc., to the exposure wavelength means low loss of the active energy ray, which provides the photosensitive resin composition having the high sensitivity.

Also, when the exposure is performed by using a high-pressure mercury-vapor lamp which is a general exposure source, the transmittance to an active energy ray which has at least one of the wavelengths of 436 nm, 405 nm and 365 nm is preferably 5% or more, more preferably 15% or more, further preferably 50% or more.

The weight average molecular weight of the polymer precursor such as the polyimide precursor or the polybenzoxazole precursor, although it depends on the application, is preferably in the range of 3,000 to 1,000,000, more preferably in the range of 5,000 to 500,000, further preferably in the range of 10,000 to 500,000. When the weight average molecular weight is less than 3,000, the strength of the coat or the film obtained from the polymer precursor is insufficient. In addition, when the polymer such as the polyimide is made by heating treatment, etc., the strength of the resultant film is poor. On the other hand, when the weight average molecular weight exceeds 1,000,000, the viscosity increases and the solubility decreases. As a result, the coat or the film having a flat surface and a uniform thickness is difficult to be obtained.

The molecular weight used herein is meant to be a value obtained by the polystyrene conversion using a gel permeation chromatography (GPC). The molecular weight may be a molecular weight of a polymer precursor itself such as a polyimide precursor, etc., or a molecular weight of a polymer precursor after chemical imidization treatment by using acetic anhydride, etc.

A solvent used in the synthesis of the polyimide precursor or the polybenzoxazole precursor is preferably a polar solvent. Examples of the representative solvent include N-methyl-2-pyrrolidone, N-acetyl-2-pyrrolidone, N,N-dimethylformamide, N,N-dimethylacetamide, N,N-diethylformamide, N,N-diethylacetamide, N,N-dimethylmethoxyacetamide, dimethyl sulfoxide, hexamethylphosphoamide, pyridine, dimethylsulfone, tetramethylenesulfone, dimethyltetramethylsulfone, diethyleneglycoldimethylether, cyclopentanone, γ-butyrolactone, α-acetyl-γ-butyrolactone, etc. These solvents are used alone or in combination of two or more. In addition to the above, examples of a usable solvent for combination include a nonpolar solvent such as benzene, benzonitrile, 1,4-dioxane, tetrahydrofuran, butyrolactone, xylene, toluene, cyclohexanone, etc. These solvents are used as a disperse medium of material, a reaction conditioning agent, or a volatilization controlling agent for a solvent from a product, and a coating smoothing agent, etc.

The polyamick acid and the polybenzoxazole precursor also have an advantage that the difference between the solubility of the exposed region and the solubility of the unexposed region in the photosensitive resin composition of the present invention is made larger by combination of lowering of solubility due to the base material generated from the photoinitiator containing the compound represented by formula (1), because the base material works to increase the molecular weight so as to lower the solubility.

The content of the polymer precursor in the photosensitive resin composition of the present invention is preferably 30% by mass or more, more preferably 50% by mass or more, to the whole solid content of the photosensitive resin composition, in view of the film properties, particularly, the film strength and the heat resistance.

Also, the content of the photopolymerization initiator containing the compound represented by formula (1) in the photosensitive resin composition of the present invention is usually 0.1 to 95% by mass, preferably 0.5 to 60% by mass to the whole solid content of the polymer precursor included in the photosensitive resin composition. When the content of the photopolymerization initiator is less than 0.1% by mass, the large difference between the solubility of the exposed region and the solubility of the unexposed region is not sufficiently made. When the content of the photosensitive resin composition exceeds 95% by mass, the properties of the cured products of the photosensitive resin composition are difficult to occur. When the base material generated by irradiation from the photopolymerization initiator containing the compound represented by formula (1) is used as a curing agent, for example, at a case using an epoxy resin, the content of the photopolymerization initiator containing the compound represented by formula (1) is usually 0.1 to 95% by mass, preferably 0.5 to 60% by mass to the whole solid content of the polymer precursor contained in the photosensitive resin composition.

When the base compound generated from the compound represented by formula (1) works as a catalyst, the content of the photopolymerization initiator containing the compound represented by formula (1) is usually 0.1 to 30% by mass, preferably 0.5 to 20% by mass to the whole solid content of the polymer precursor contained in the photosensitive resin composition.

<Other Components>

The photosensitive resin composition of the present invention may be a simple mixture of the photopolymerization initiator containing the compound represented by formula (1) and the polymer precursor, but, may further include other components such as a solvent, a photocurable or a thermosetting component, a non-polymeric binder resin except for the polymer precursor.

As a solvent for dissolving, dispersing or dilute the photosensitive resin composition, various general-purpose solvents can be used. Also, when polyamic acid is used as a polymer precursor, solution provided by a synthesis reaction of the polyamic acid may be just used as it is and may be mixed with the photopolymerization initiator including the compound represented by formula (1), and optional other components as necessary.

Examples of the available solvent used widely include ethers such as diethyl ether, tetrahydrofuran, dioxane, ethylene glycol dimethyl ether, ethylene glycol diethyl ether, propylene glycol dimethyl ether, propylene glycol diethyl ether and diethylene glycol dimethyl ether; glycol monoethers (so-called cellosolves) such as ethylene glycol monomethyl ether, ethylene glycol monoethyl ether, propylene glycol monomethyl ether, propylene glycol monoethyl ether, diethylene glycol monomethyl ether and diethylene glycol monoethyl ether; ketones such as methyl ethyl ketone, acetone, methyl isobutyl ketone, cyclopentanone and cyclohexanone; esters such as ethylacetate, butylacetate, n-propylacetate, i-propylacetate, n-butylacetate, i-butylacetate, ester acetate of glycolmonoeters (e.g., methyl cellosolve acetate, ethyl cellosolve acetate), propylene glycol monomethyl ether acetate, propylene glycol monoethyl ether acetate, dimethyl oxalate, methyl lactate and ethyl lactate; alcohols such as ethanol, propanol, butanol, hexanol, cyclohexanol, ethylene glycol, diethylene glycol and glycerin; halogenated hydrocarbons such as methylene chloride, 1,1-dichloroethane, 1,2-dichloroethylene, 1-chloropropane, 1-chlorobutane, 1-chloropentane, chlorobenzene, bromobenzene, o-dichlorobenzene and m-dichlorobenzene, an amides such as N,N-dimethylformamide, N,N-diethylformamide, N,N-dimethylacetamide, N,N-diethyl acetamide and N,N-dimethylmethoxyacetamide; pyrrolidones such as N-methyl-2-pyrrolidone and N-acetyl-2-pyrrolidone; lactones such as γ-butyrolactone and α-acetyl-γ-butyrolactone, sulfoxides such as dimethyl sulfoxide; sulfones such as dimethyl sulfone, tetramethylene sulfone and dimethyl tetramethylene sulfone; phosphate amides such as hexamethyl phosphoamide, other organic polarity solvents. Besides, aromatic hydrocarbons such as benzene, toluene, xylene, pyridine, and other organic non-polar solvents may be used. These solvents are used alone or in combination.

Among them, polar solvents such as propylene glycol monomethyl ether, methyl ethyl ketone, cyclopentanone, cyclohexanone, ethylacetate, propylene glycol monomethyl ether acetate, N,N-dimethyl acetamide, N-methyl-2-pyrrolidone and γ-butyrolactone; aromatic hydrocarbons such as toluene; and mixing solvents comprising these solvents are preferably used.

The photosensitive resin composition of the present invention may contain a photocurable component. As a photocurable component, a compound having one or two or more ethylenically unsaturated bonds may be used. Examples of the photocurable component include an amide monomer, (meta)acrylate monomer, an urethane(meta)acrylate oligomer, a polyester(meta)acrylate oligomer, epoxy (meta)acrylate, and a hydroxyl group containing (meta) acrylate, aromatic series vinyl compounds such as styrene. In a case where the polyimide precursor has a carboxylic component such as polyamic acid in the structure, an ionic bond is formed by the compound having the ethylenically unsaturated bond having a tertiary amino group with the carboxylic acid of the polyimide precursor so as to make the large contrast of the solubility speed of the exposed region and the solubility of the unexposed region in the photosensitive resin composition.

In the photosensitive resin composition of the present invention, a photopolymerization initiator (photobase generator) except for the photopolymerization initiator containing the compound represented by formula (1) may be used together.

The photopolymerization initiator which can be used together is not particularly limited, for example, light radical polymerization initiator may be used. As a light radical polymerization initiator, any compounds may be used as long as the compound may provide a radical by light, laser, electron beam, etc., to start the radical polymerization reaction.

Examples of the photopolymerization initiator which can be used together include benzoin and benzoin alkyl ethers such as benzoin, benzoin methyl ether, benzoin ethyl ether and benzoin isopropyl ether; alkyl phenones such as 2-hydroxy-2-methyl-1-phenyl-propan-1-one; acetophenones such as acetophenone, 2,2-dimethoxy-2-phenyl acetophenone, 2,2-diethoxy-2-phenylacetophenone, and 1,1-dichloroacetophenone; aminoacetophenones such as 2-methyl-1-[4-(methylthio)phenyl]-2-morpholinopropan-1-one, 2-benzyl-2-dimethylamino-1-(4-morpholinophenyl)-butan-1-one and N,N-dimethylaminoacetophenone; anthraquinones such as 2-methylanthraquinone, 2-ethylanthraquinone, 2-t-butylanthraquinone and 1-chloroanthraquinone; thioxanthones such as 2,4-dimethylthioxanthone, 2,4-diethylthioxanthone, 2-chlorothioxanthone, and 2,4-diisopropylthioxanthone; ketals such as acetophenone dimethylketal and benzyldimethylketal; 2,4,5-triarylimidazole dimer; riboflavin tetrabutylate; thiol compounds such as 2-mercaptobenzimidazole, 2-mercaptobenzoxazole and 2-mercaptobenzothiazole; organohalogens such as 2,4,6-tris-s-triazine, 2,2,2-tribromoethanol and tribromomethylphenyl sulfone; benzophenones or xanthones such as benzophenone and 4,4'-bisdiethylamino benzophenone; acylphosphine oxides such as 2,4,6-trimethylbenzoyldiphenylphosphine oxide and bis(2,4,6-trimethylbenzoyl)-phenylphosphine oxide; titanocenes such as bis(cyclopentadienyl)diphenyl titanium, bis(cyclopentadienyl)dichlorotitanium, bis(cyclopentadienyl)-bis(2,3,4,5,6-pentafluorophenyl) titanium and bis(cyclopentadienyl)-bis(2,6-difluoro-3-(pyrrol-1-yl)phenyl) titanium.

These well-known conventional photopolymerization initiators can be used alone or as a mixture of two or more, besides, photoinitiating aids such as a tertiary amines such as N,N-dimethyl aminobenzoic acid ethyl ester, N,N-dimethylamino benzoic acid isoamyl ester, pentyl-4-dimethylaminobenzoate, triethylamine and triethanolamine can be added.

Examples of the commercially available photopolymerization initiator include Irgacure 261, 184, 369, 651, 500, 819, 907, 784, 2959, Darocur 1116, 1173, CGI1700, CGI1750, CGI1850, CG-24-61, Lucirin TPO, CGI-784 (product names; manufactured by BASF Japan Ltd.), DAICATII (product names; manufactured by Daicel Chemical Industries Corporation), UVAC1591 (product names; manufactured by Daisel UCB company), Roadsillphotoinitiator 2074 (product names; manufactured by Rodel, Inc.), Ubecryl P36 (product names; manufactured by UCB S.A.), Ezacure KIP150, KIP65LT, KIP100F, KT37, KT55, KTO46, KIP75/B, and ONE (product names; manufactured by Fratelli-Lamberti).

When the photopolymerization initiator which can be used together is used, formulation ratio of photopolymerization initiator which can be used together is in a range of 0.5 to 10 parts by mass in the photosensitive resin composition of the present invention of 100 parts by mass which is preferable.

A photobase generator except for formula (1) may be used by replacement of the above photopolymerization initiator or in addition to the above photopolymerization initiator together. The photobase generator is a compound capable of producing one or more base compounds which may work as a catalyst for additional reaction of (meta)acrylate having an epoxy group with a thermal curing component by change of molecule structure or by the cleavage of molecule by irradiation of rays such as ultraviolet rays or visible light. Examples of the base material generated include a secondary amine and a tertiary amine.

Examples of the photobase generator which can be used together include an α-amino acetophenone compound, an oxime ester compound, and compounds having substituents such as an acyl oxyimino group, a N-formilation aromatic amino group, a N-acylation aromatic amino group, a nitro benzyl carbamate group or an alkoxybenzyl carbamate group. Among them, an oxime ester compound and an α-amino acetophenone compound are preferable. As an α-amino acetophenone compound, the compound having two or more nitrogen atoms is particularly preferable. As other photobase generators, WPBG-018 (product name; 9-anthrylmethyl N, N'-diethylcarbamate, manufacture by Wako Pure Chemical Industries Ltd.), WPBG-027 (product name; (E)-1-[3-(2-hydroxyphenyl)-2-propenoyl]piperidine), WPBG-082 (product name: guanidinium 2-(3-benzoylphenyl)propionate), WPBG-140 (product name; 1-(anthraquinon-2-yl)ethylimidazolecarboxylate), etc., can also be used. An α-amino acetophenone compound has a benzoin ether bond in the molecule, which provides cleavage in the molecule by irradiation to produce a base material (amine), which works as a curing catalyst. Specifically, examples of the α-amino acetophenone include commercial compounds or solutions thereof such as 4-morpholino benzoyl-1-benzyl-1-dimethylamino propane (Irgacure 369, product name, manufactured by BASF Japan Ltd.) and 4-(methylthiobenzoyl)-1-methyl-1-morpholino ethane (Irgacure 907, product name, manufactured by BASF Japan Ltd.), 2-(dimethylamino)-2-[(4-methylphenyl)methyl]-1-[4-(4-morpholinyl)phenyl]-1-butanone (Irgacure 379, product name, manufactured by BASF Japan Ltd.)

As an oxime ester compound which can be used together, any oxime ester compounds can be used as long as the compound can produce a base material by irradiation. Examples of the oxime ester which may be commercially available include CGI-325, Irgacure OXE01 and Irgacure OXE02 manufactured by BASF Japan Ltd, and N-1919 and NCI-831 manufactured by ADEKA CORPORATION. Also, the compound having two oxime ester groups in the molecule can be preferably used which is described in Japanese Patent No. 4344400.

In addition, examples include carbazole oxime ester compounds described in JP2004-359639A, JP2005-097141A, JP2005-220097A, JP2006-160634A, JP2008-094770A, JP2008-509967T, JP2009-040762T and JP2011-80036A.

A base propagating agent which can generate a base by decomposition or transfer reaction due to a little amount of the base generated from the base generator. Examples of the base propagating agent include a compound having a 9-fluorenylmethyl carbamate bond, a compound having a 1,1-dimethyl-2-cyanomethylcarbamate bond $((CN)CH_2C(CH_3)_2OC(O)NR_2)$, a compound having para-nitrobenzylcarbamate bond, a compound having a 2,4-dichlorobenzyl carbamate bond, in addition to those, examples also include a urethane compound described in paragraphs 0010 to 0032 of JP 2000-330270A and a urethane compound described in paragraphs 0033 to 0060 of JP 2008-250111A.

The addition of a sensitizer may show advantageous effects to improve the sensitivity by allowing the base generator to sufficiently use the energy of active energy ray permeating the polymer. Particularly, the effect provided by the addition of the sensitizer is large, when the polyimide precursor also has absorption in a wavelength of 360 nm or more. The examples of the compound called a sensitizer include thioxanthone, diethylthioxanthone and the derivatives thereof, a coumarin and the derivatives thereof, a ketocoumarin and the derivatives thereof, a keto biscoumarin and the derivative thereof, cyclopentanone and the derivative thereof, cyclohexanone and the derivative thereof, thiopyrylium salt and the derivative thereof, and thioxanthene, xanthene and the derivatives thereof. Specifically, examples of the coumarin, the ketocoumarin and the derivatives thereof include 3,3'-carbonylbiscoumalin, 3,3'-carbonylbis(5,7-dimethoxy coumarin) and 3,3'-carbonylbis(7-acetoxy coumarin). Specifically, examples of the thioxanthone and the derivatives thereof include diethyl thioxanthone, isopropyl thioxanthone. Furthermore, examples also include benzophenone, acetophenone, phenanthrene, 2-nitro fluorene, 5-nitroacenaphthene, benzoquinone, 2-ethylanthraquinone, 2-tert-butylanthraquinone, 1,2-benz anthraquinone and 1,2-naphthoquinone. The sensitizer showing the most suitable sensitization working is selected appropriately, because the above sensitizer shows particularly superior effects generated by the combination with the base generators.

Various organic or inorganic compounds having a small molecule or a large molecule may be formulated in order to give processing properties or various kinds of functionalities to the photosensitive resin composition of the present invention. For example, a dye, a surfactant, a leveling agent, a plasticizer, fine particles can be used. The fine particles include organic fine particles such as polystyrene and poly-tetrafluoroethylene, fine inorganic particles such as colloidal silica, carbon and layered silicate, which may be porous or hollow structures. Also, a pigment, a filler and fiber, etc., are the functions or the forms thereof.

Formulation ratio of the optional components except for solvents is preferably in a range of 0.1 to 95% by mass to the whole solid content of the photosensitive resin composition. When formulation ratio is less than 0.1% by mass, the effect of the addition of the additives is difficult to appear. When formulation ratio exceeds 95% by mass, the characteristic of the resin cured product is difficult to be reflected in the final products.

The photosensitive resin composition of the present invention may be used by various coating processes and forming processes so as to manufacture a film or a formed body having a three-dimensional shape, etc.

When the polyimide precursor and the polybenzoxazole precursor are used as a polymer precursor in one embodiment of the photosensitive resin composition of the present invention, a 5% weight reduction temperature which is obtained by the measurement of the polyimide or the polybenzoxazole in a nitrogen atmosphere is preferably 250° C. or more, more preferably 300° C. or more in view of securing the heat resistance, the dimensional stability, and the insulation. In particular, in the use for applications such as electronic components including a solder reflow step, when the 5% weight reduction temperature is 300° C. or less, failure such as bubbles due to the decomposition gas generated in the solder reflow step is possible to occur.

The higher the glass transition temperature of the polyimide and the polybenzoxazole obtained from the photosensitive resin composition of the present invention is, the better it is in view of the heat resistance. In the applications including a heat forming process such as the formation of light waveguide, the glass transition temperature is preferably about 120 to 450° C., more preferably, the glass transition temperature is about 200 to 380° c.

The glass transition temperature in the present invention is obtained from a peak temperature of tan δ (tan δ=loss elasticity coefficient (E")/storage elasticity coefficient (E')) by using the dynamic viscoelasticity measurement, when the polyimide and the polybenzoxazole provided from a photosensitive resin composition can be made into a film shape.

The dynamic viscoelastic measurement is performed by using a viscoelastic measuring device. The dynamic viscoelasticity measurement can be conducted, for example, by Solid Analyzer RSAII (manufactured by Rheometric Scientific Ltd.) at a frequency of 3 Hz, and at a rising temperature rate of 5° C./min. When the polyimide and the polybenzoxazole obtained from the photosensitive resin composition cannot be formed into a film shape, the glass transition temperature is determined by identifying a temperature of the inflection point of baseline of the differential thermal analysis (DTA).

From the viewpoint of the dimensional stability of the polyimide and the polybenzoxazole film obtained from the photosensitive resin composition of the present invention, a linear thermal expansion coefficient is preferably 60 ppm or less, more preferably 40 ppm or less. In the production process for a semiconductor device, etc., when a film is formed on a silicon wafer, 20 ppm is further preferable from the viewpoint of adhesion and warpage of substrate.

The linear thermal expansion coefficient of the film of the polyimide and the polybenzoxazole in the present invention can be obtained by using a thermomechanical analyzer device (TMA). The linear thermal expansion coefficient can be obtained by using a thermomechanical analyzer (for example, Thermo Plus TMA8310 manufactured by Rigaku corporation) at a rising temperature rate of 10° C./min and at a tensile loading of 1 g/25000 μm$^2$ so that the loading per a cross-sectional area of an assessment sample can be the same.

As described above, because according to the present invention, the photosensitive resin composition can be obtained by an easy method including only mixing the photopolymerization initiator containing the compound represented by formula (1) with the polymer precursor, the composition is superior in cost performance. Because an aromatic component containing carboxylic acid and a basic material constituting the photopolymerization initiator containing the compound represented by formula (1) is available inexpensively, the price of the photosensitive resin composition can be suppressed. The photopolymerization initiator containing a compound represented by formula (1) may be used for reaction acceleration from various polymer precursor to the final products, and the structure of the polymer which is finally obtained can be widely selected. Furthermore, by catalytic effects of the base material of the amines generated from irradiation of the active energy ray, the treatment temperature needed for the reactions such as cyclization such as imidization for the final product from, for examples, the polyimide precursor and the polybenzoxazole precursor can decrease to reduce the load for process and the thermal damage of the products. Moreover, the base generator in the present invention generates base by irradiation of the active energy ray and heating, when the steps for producing the final product from the polymer precursor include a heating step, the base generator of the present invention uses the heating step to reduce the amount of the irradiation of the active energy ray, that is, the steps can be economically used.

The photosensitive resin composition of the present invention is suitably used for all of known fields and products using a printing ink, a paint, a sealant, an adhesive, an electronic material, a light circuit component, a forming material, a resist material, a construction material, a photoforming product, an optical component, and a resin material. The photosensitive resin composition can be used not only for the applications needed for entire exposure such as a paint, a sealant and an adhesive, but also for the applications needed for pattern forming such as a permanent film and a peeling film.

The photosensitive resin composition of the present invention is suitably used for the wide fields and the products required for the heat resistance, the dimensional stability and the insulation, for example, a paint, a printing ink, a sealant, an adhesive or a display device, a semiconductor device, an electronic part, a microelectro mechanical system (Micro Electro Mechanical System (MEMS)), a photoforming product, an optical component or a construction material. Specifically, examples of forming materials for electronic parts include a sealing material, and examples of layer forming materials include materials for a printed circuit board, an interlayer insulation film and a circuit coating film. In forming materials for display device, the composition may be used for a color filter, a film for flexible display, a resist material and an alignment film, as a layer forming material and an image forming material. As a forming material for a semiconductor device, the composition may be used for a resist material and a forming material for buffer coating film. In a forming material for an optical component, the composition may be used for a hologram, an optical waveguide, an optical circuit, an optical circuit component, an anti-reflection coat as an optical material and a layer forming material. For construction materials, the composition may be used for a paint and a coat. Also, the composition may be used as a material for an optical shaping. By using the photosensitive resin composition, any of a printed matter, a paint, a sealant, adhesive, a display device, a semiconductor device, an electronic part, a microelectronic mechanical system, an optical shaped material, an optical component or a construction material are provided.

Because the photosensitive resin composition of the present invention has features as described above, the photosensitive resin composition can be used as materials for a pattern forming material. Particularly, the photosensitive resin composition containing a polyimide precursor or a polybenzoxazole precursor is used as a pattern forming material (resist), the pattern formed by using the composition works as a permanent film of the polyimide or the polybenzoxazole, which is a component for providing the heat resistance and the insulation. It is suitable for the formation of a color filter, a film for flexible display, an electronic part, a semiconductor device, an interlayer insulating film, a wiring coating film, a light circuit, a light circuit component, an anti-reflection coat, other optical components or electronic members.

<Patterning Method>

The pattern forming method of the present invention is characterized by forming a coat or a formed body of the photosensitive resin compositions of the present invention, irradiating an activity energy ray to the coat or the formed body in a predetermined pattern form, heating after the irradiation or at the same time of irradiation so as to change the solubility of the irradiated area, followed by development.

A radical and a base material are produced by opening the photopolymerization initiator containing the compound represented by formula (1) only in the irradiated area by applying the photosensitive resin composition of the present invention on a substrate or forming a formed body by using a suitable forming method, and irradiating the coat or the formed body with the active energy ray and heating the coat and the formed after the irradiation or at the same time of the irradiation. The base material works as a catalyst for acceleration for the molecular weight increase reaction of the polymer precursor in the irradiated area.

When the polymer precursor reducing the curing temperature by catalytic effect, such as a polyimide precursor or a polybenzoxazole precursor, is used, the area to be kept of the coat or the formed body of the photosensitive resin composition obtained by combining this polymer precursor with the photopolymerization initiator including the compound represented by formula (1) is exposed, firstly. The base material generated by the irradiation or the heating at the same time of the irradiation selectively reduces the thermal-curing temperature of the exposed area. The exposed area is cured, after the exposure or at the same time of the exposure at a temperature at which the exposed are is cured and the unexposed are is not cured. The heat treatment for generating a base material and the heat treatment for curing only the exposed area (bake after exposure) may be made into the same step or the different steps. Next, by dissolving the unexposed are with the predetermined developer such as organic solvents and basic aqueous solutions, the pattern of thermal-cured product is formed. The pattern is subjected to optional heat treatment to complete the thermal curing, if necessary. By the steps mentioned above, the predetermined two-dimensional resin pattern (general planar pattern) or the three-dimensional resin pattern (sterically formed shape) which is a usual negative type can be obtained.

When a polymer precursor which starts the reaction by catalytic effects of the base, such as a compound or a polymer having an epoxy group and a cyanate group, the area to be kept of the coat or the formed body of the photosensitive resin composition obtained by combining this polymer precursor with the photopolymerization initiator including the compound represented by formula (1) is exposed, firstly. By a radical and a basic material generated by the exposure or at the same time of the exposure, the molecular weight increasing reaction of the compound having an acryloyl group, an epoxy group or a cyanate group occurs to cure only the exposed area. The heat treatment for generating a base material and the heat treatment for curing only the exposed area (bake after exposure) may be made into the same step or the different steps. Next, by dissolving the unexposed are with the predetermined developer such as organic solvents and basic aqueous solutions, the pattern of thermal-cured product is formed. The pattern is subjected to optional heat treatment to complete the thermal curing, if necessary. By the steps mentioned above, the predetermined two-dimensional resin pattern (general planar pattern) or the three-dimensional resin pattern (sterically formed shape) which is a usual negative type can be obtained. By the steps mentioned above, the predetermined two-dimensional resin pattern (general planar pattern) or the three-dimensional resin pattern (sterically formed shape) which is a usual negative type can be obtained.

The photosensitive resin composition of the present invention can provide a coat which does not have stickiness on the surface of the substrate by dissolving the photosensitive resin composition in a polar solvent such as propylene glycol monomethyl ether, methylethyl ketone, cyclopentanone, cyclohexanone, ethylacetate, propylene glycol monomethyl ether acetate, N,N-dimethylacetamide, N-methyl-2-pyrrolidone and γ-butyrolactone; aromatic hydrocarbons such as toluene; a mixing solvent containing the above solvents, subsequently, applying the solution containing the photosensitive resin on a substrate such as a silicon wafer, a metal substrate, a ceramic substrate and a resin film, by an immersion method, a spray method, a flex printing method, a gravure printing method, a screen printing method, a spin coating method and a dispense method, and largely removing the solvent by heating. The thickness of the coating film is not particularly limited, but the thickness is preferably 0.5 to 50 µm. In view of the sensitivity and developing speed, 1.0 to 20 µm is more preferably. The dry conditions of the applied coat are 1 to 20 minutes at 80 to 100° C.

An active energy ray is irradiated to the coat through a mask having a predetermined pattern to conduct an exposure in the pattern. After the heating, the unexposed area is removed by developing using a suitable developer to form a film having a predetermined pattern.

An exposure method and an exposure device used for the exposure step are not limited, and the contact exposure and the indirect exposure can be performed. A contact/proximity exposure apparatus using a g-ray stepper, an i-ray stepper and a super pressure mercury lamp, a mirror projection exposure apparatus or other projector and light source capable of irradiating ultraviolet rays, a visible ray, an X-ray, and an electron ray.

The heating temperature for generating a base by removing a protection group by heating before, after or at the same time of exposure is appropriately selected according to the polymer precursor for combination or purpose, therefore, is not particularly limited. The heating may be conducted by the temperature of the circumstance of the place where the photosensitive resin composition is arranged (for example, a room temperature). In that case, the base is gradually generated. Because the base is also generated by the heat sub-generated at the irradiation of the active energy ray, the heating may be substantially conducted by the heat sub-generated at the irradiation of the active energy ray. From the viewpoint of producing amine efficiently, the heating temperature is preferably 30° C. or more, more preferably 60° C. or more, further preferably 100° C. or more, particularly preferably 120° C. or more. However, a polymer precursor used together for combination may also be cured in the unexposed area at 60° C. or more, the suitable temperature is not limited to the above. For example, in the case of epoxy resin, the temperature is appropriately selected, but preferable temperature of heating treatment is usually 100 to 150° C.

Only deprotection by removing a protection group may be conducted by heating before the exposure. The heating for deprotection by removing the protection group before the irradiation of the active energy ray may be conducted in the drying step of the coat, or in other heating step. In this case, the heating temperature may be appropriately selected, as long as the deprotection may be performed. The heating temperature is preferably 50 to 180° C., and the heating time is preferably 10 seconds to 60 minutes.

In order to physically accelerate a cross-linking reaction, and to react to cure the exposed area only, the post exposure bake (PEB) of the coat of the photosensitive resin composition may be conducted between the exposure step and the development step. The PEB is preferably conducted at a temperature at which the reaction rates of the curing reactions of imidization, etc., in the unexposed area where no basic compound is generated and in the exposed area where the basic compound is generated due to the irradiation of the active energy ray and the heating are different. For example, in the imidization, the preferable heating treatment is usually around 60 to 200° C., the more preferably 120 to 200° C. When the heating treatment temperature is less than 60° C., imidization effects are poor, and therefore, it is difficult to make the difference of imidization rates in the exposed area and in the unexposed area under the practical process conditions. When the heating treatment temperature is exceeds 200° C., the imidization in the unexposed area containing no amine may also proceed, resulting in hardly making difference of solubility of the exposed area and the unexposed area. The heat treatment is conducted by any conventional methods such as methods using a circulation oven and a hot plate in the atmosphere of air or nitrogen atmosphere, but the heat treatment is not limited to these. This heat treatment for generating the basic compound and the PEB treatment are made in the same step or different steps.

(Developer)

The developer used for the developing step is not limited as long as a solution or a solvent which can dissolve the unexposed parts selectively. The developer can be appropriately selected from basic solutions and organic solvents, etc., according to the polymer precursor.

The basic aqueous solution as a developer is not particularly limited. Examples of the basic aqueous solution include a tetramethylammonium hydroxide (TMAH) aqueous solution having a concentration of 0.01 to 10% by mass, preferably 0.05 to 5% by mass, furthermore, a solution having a solute such as diethanolamine, diethylaminoethanol, sodium hydroxide, potassium hydroxide, sodium carbonate, potassium carbonate, sodium hydrogen carbonate, potassium hydrogen carbonate, triethylamine, diethylamine, methylamine, dimethylamine, acetic acid dimethyl aminoethyl, dimethyl aminoethanol, dimethylaminoethyl methacrylate, cyclohexylamine, ethylenediamine, hexamethylene diamine and tetramethyl ammonium.

These solutes may be used alone, or in mixture of two or more. The developer may contain an organic solvent, etc., as long as the content of water in the developer is 50% or more, preferably 70% or more.

The organic solvent as a developer is not limited. As an organic solvent, polar solvents such as N-methyl-2-pyrrolidone, N,N-dimethylformamide, N,N-dimethyl acetamide, dimethyl sulfoxide, γ-butyrolactone and dimethyl acrylamide; alcohols such as methanol, ethanol and isopropanol; esters such as ethylacetate and propylene glycol monomethyl ether acetate; ketones such as cyclopentanone, cyclohexanone, isobutyl ketone and methyl isobutyl ketone; tetrahydrofuran; chloroform; or acetonitrile may be used alone or in mixture of two.

After the development, washing is conducted with water or a poor solvent. In this case, alcohols such as ethanol and isopropyl alcohol, or esters such as lactic acid ethyl and propylene glycol monomethyl ether acetate may be added to the water.

After the washing, dry is performed at 80 to 100° C. to stabilize the pattern. In order to make this relief pattern have heat resistance, heating is performed at a temperature of 180 to 500° C., preferably 200 to 350° C. for from several tens of minutes to several hours to form a high heat resistance resin layer having the pattern.

EXAMPLES

The present invention now will be described in more detail with reference to Examples, but these Examples are only for the purpose of suitably illustrating the present invention and are not intended to limit the present invention by any means. Parts in Synthesis Examples and Examples each represent parts by mass.

Example 1 Synthesis of Compound Represented by Formula (1) of the Present Invention (Step 1) Synthesis of Intermediate Compound Represented by Formula (12)

To a flask equipped with a stirrer, a reflux condenser, and a stirring device, 9.0 parts of paraformaldehyde and 170 parts of dimethyl sulfoxide were added and stirred. A solution of 1.4 parts of potassium hydroxide dissolved in 5 parts of ethanol was added dropwise to the flask, and the mixture was stirred until paraformaldehyde completely dissolved. A solution of 50 parts of a benzoin represented by the following formula (11) dissolved in 30 parts of dimethyl sulfoxide was added dropwise to the flask over 30 minutes, and the mixture was stirred at room temperature for 2 hours. Thereafter, 2.6 parts of 35% hydrochloric acid was added dropwise thereto for neutralization to terminate the reaction. Toluene and saturated saline were added to this reaction solution to perform extraction into the organic layer, and the solvent was distilled off. The concentrated reaction liquid was crystallized to obtain 40 parts of the intermediate compound represented by the following formula (12).

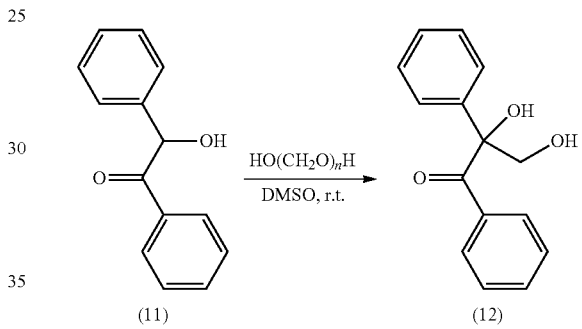

(Step 2) Synthesis of Compound of the Present Invention Represented by the Following Formula (A-1)

(Photopolymerization Initiator 1)

12.0 parts of the intermediate compound represented by formula (12) obtained in the step 1, 100 parts of toluene, and 0.08 part of tin octylate were added to a flask and stirred under reflux to homogeneity. Subsequently, 6.5 parts of dicyclohexylmethane-4,4-diisocyanate was added under reflux. After reflux was continued for 3 hours, the solution was cooled, and the solvent was distilled off by an evaporator. A brown solution obtained was added dropwise to cyclohexane, and the mixture was washed by stirring for 30 minutes to obtain 10.0 parts of the compound of the present invention represented by the following formula (A-1) (photopolymerization initiator 1).

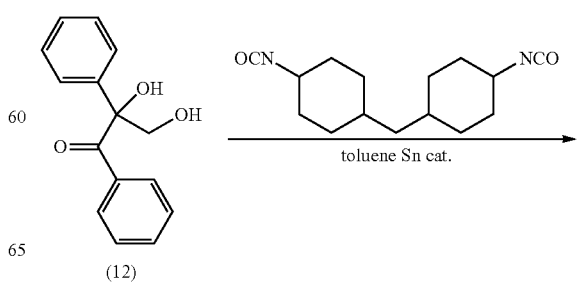

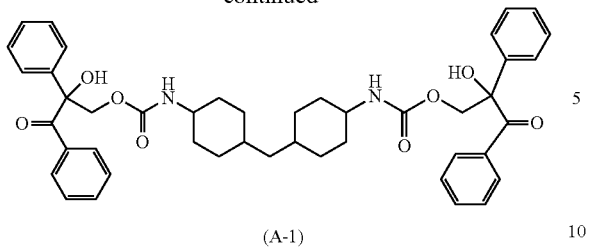

(A-1)

Example 2 Synthesis of Compound Represented by Formula (1) of the Present Invention (Step 3) Synthesis of Intermediate Compound Represented by Formula (14)

The same procedure as in the step 1 was repeated except that an anisoin represented by the following formula (13) was used instead of the benzoin to obtain 8.5 parts of the intermediate compound represented by the following formula (14).

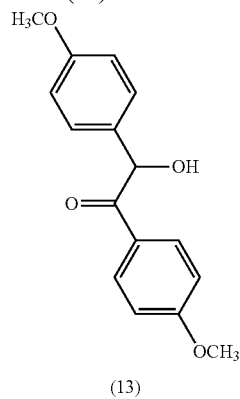

(13)

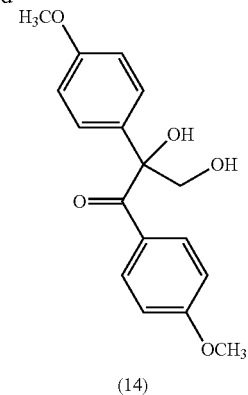

(14)

(Step 4) Synthesis of Compound of the Present Invention Represented by the Following Formula (A-2)

(Photopolymerization Initiator 2)

12.0 parts of the intermediate compound represented by formula (14) obtained in the step 3, 100 parts of toluene, and 0.08 parts of tin octylate were added to a flask and stirred under reflux to homogeneity. Subsequently, 6.5 parts of dicyclohexylmethane-4,4'-diisocyanate was added under reflux. After reflux was continued for 3 hours, the solution was cooled, and the solvent was distilled off by an evaporator. A brown solution obtained was added dropwise to cyclohexane, and the mixture was washed by stirring for 30 minutes to obtain 10.0 parts of the compound of the present invention represented by the following formula (A-2) (photopolymerization initiator 2).

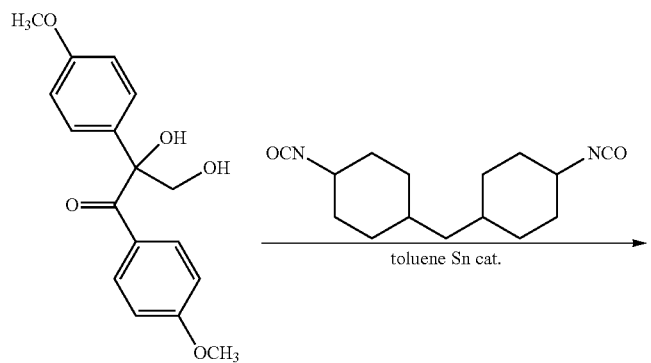

(14)

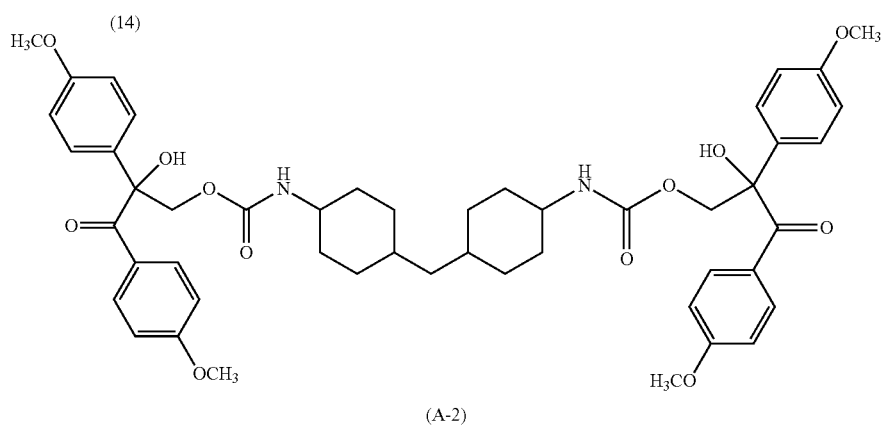

(A-2)

<Synthesis of Compound for Comparison>
(Step 5) Synthesis of Compound for Comparison Represented by the Following Formula (A-3) (Photopolymerization Initiator 3)

The same procedure as in the step 4 was repeated except that hexamethylene diisocyanate was used instead of dicyclohexylmethane-4,4'-diisocyanate to obtain 2.5 parts of the compound for comparison represented by the following formula (A-3) (photopolymerization initiator Photopolymerization initiator 1: photopolymerization initiator 1 obtained in Example 1
Photopolymerization initiator 2: photopolymerization initiator 2 obtained in Example 2
Photopolymerization initiator 3: photopolymerization initiator 3 obtained in Comparative Synthesis Example 1
Photopolymerization initiator 4: IRGACURE OXE01 (manufactured by BASF, oxime ester-type compound)

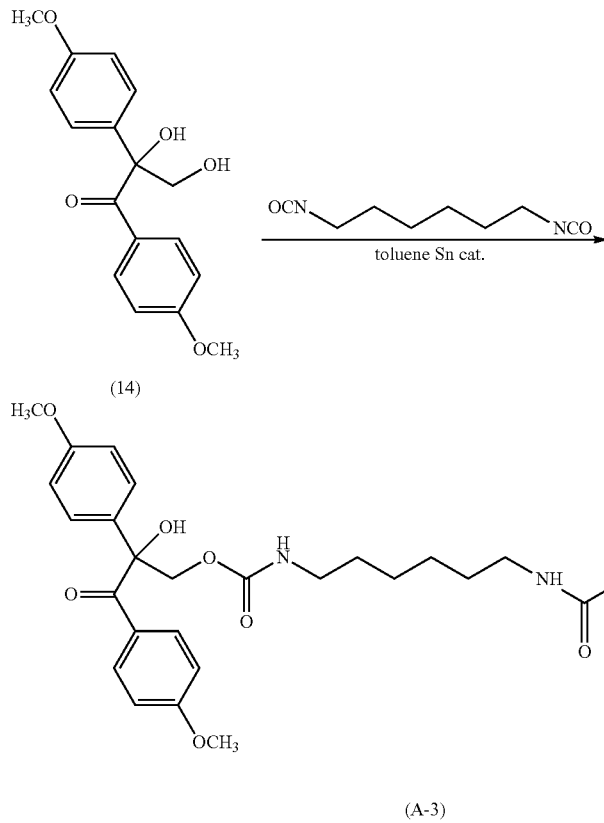

Examples 3 to 4, Comparative Examples 1 to 2

(Preparation of Photosensitive Resin Composition)

Respective components were mixed in accordance with the amounts to be blended listed in Table 1 to obtain photosensitive resin compositions.

TABLE 1

Composition of photosensitive resin compositions

| | Example 3 | Example 4 | Comparative Example 1 | Comparative Example 2 |
|---|---|---|---|---|
| SU-8 resin | 100 | 100 | 100 | 100 |
| Photopolymerization initiator 1 | 10 | | | |
| Photopolymerization initiator 2 | | 10 | | |
| Photopolymerization initiator 3 | | | 10 | |
| Photopolymerization initiator 4 | | | | 10 |
| Solvent (PGMEA) | 101.5 | 101.5 | 101.5 | 101.5 |

SU-8 resin: manufactured by NIPPON KAYAKU Co., Ltd., bisphenol A novolac-type epoxy compound)
Solvent: polyethylene glycol monomethyl ether acetate (PGMEA)
(Experiment for Curing Photosensitive Resin Composition)

Each of the resin compositions of Examples 3 and 4 and Comparative Examples 1 and 2 was coated onto a Si substrate by a spin coater and then, dried by prebaking at 100° C. for 2 minutes using a hot plate to obtain a resin composition layer having a film thickness of 10 μm. Thereafter, a belt conveyor-type exposure machine mercury lamp was used for exposure to irradiate the layer with UV light of 0 to 1370 mJ/cm$^2$ (254 nm). After baked with a hot plate, the layer was subjected to development treatment by an immersion method using a development liquid. The amount of exposure when the layer was cured to be a remaining film was evaluated as sensitivity. The evaluation conditions and sensitivities at this time are listed in Table 2.

TABLE 2

Evaluation results of photosensitive resin compositions

| | | Example 3 | Example 4 | Comparative Example 1 | Comparative Example 2 |
|---|---|---|---|---|---|
| Evaluation conditions | Heating temperature | | | 110° C. | |
| | Heating time | | | 10 min | |
| | Development | | | PGMEA 1 min | |
| Evaluation results | Remaining film | 820 | 820 | 1096 | 1370 |
| | sensitivity at 254 nm (mJ/cm$^2$) | | | | |

Example 5 Synthesis of Compound Represented by Formula (1) of the Present Invention (Step 6) Synthesis of Intermediate Compound Represented by Formula (32)

To 115 parts of dimethyl sulfoxide, 10.5 parts of potassium cyanide was added, and the mixture was stirred for 15 minutes at room temperature under nitrogen atmosphere and in the presence of ultrasonic wave. To this dimethyl sulfoxide solution, 10 parts of 4-fluorobenzaldehyde represented by the following formula (31) was added dropwise, and the mixture was stirred at room temperature for 30 minutes. The reaction liquid obtained was diluted with an excess of water and extracted with toluene three times to obtain a toluene layer containing the target compound. After the toluene solution was dried over magnesium sulfate, the solvent was distilled off by an evaporator. Thereafter, the concentrate was cooled to recrystallization to obtain 14 parts of the intermediate compound represented by the following formula (32).

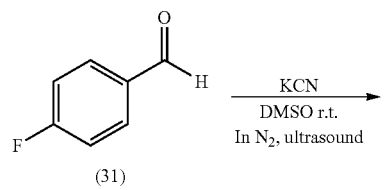

(31)

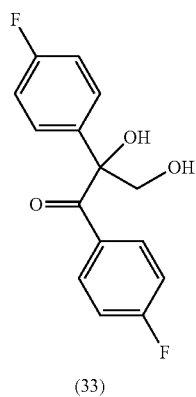

(32)

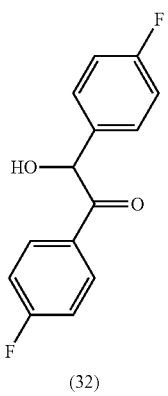

(32)

(Step 7) Synthesis of Intermediate Compound Represented by Formula (33)

The same procedure as in the step 1 was repeated except that the intermediate compound represented by the following formula (32) was used instead of the benzoin to obtain 8.1 parts of the intermediate compound represented by the following formula (33).

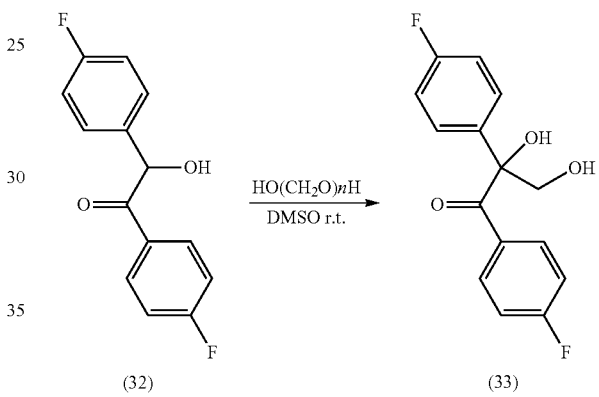

(32) (33)

(Step 8) Synthesis of Compound of the Present Invention Represented by the Following Formula (A-4) (Photopolymerization Initiator 5)

1.0 part of the intermediate compound represented by formula (33) obtained in the step 7, 30 parts of toluene, and 0.04 part of tin octylate were added to a flask and stirred under reflux to homogeneity. Subsequently, 1.1 parts of dicyclohexylmethane-4,4'-diisocyanate was added under reflux. After reflux was continued for 3 hours, the solution was cooled, and the solvent was distilled off by an evaporator. A brown solution obtained was added dropwise to cyclohexane, and the mixture was washed by stirring for 30 minutes to obtain 0.8 parts of the compound of the present invention represented by the following formula (A-4) (photopolymerization initiator 5).

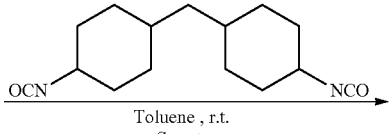

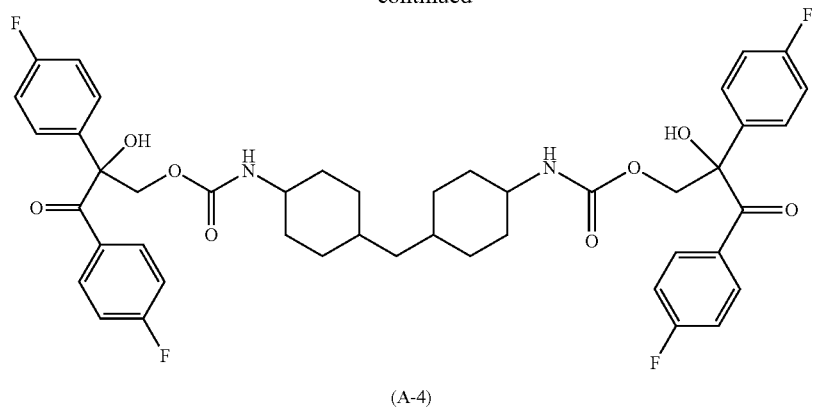

(A-4)

Example 6 Synthesis of Compound Represented by Formula (1) of the Present Invention (Step 9) Synthesis of Intermediate Compound Represented by Formula (35)

After 1.9 parts of potassium cyanide was dissolved by addition of 10 parts of water and 53 parts of ethanol, the solution was sonicated under nitrogen atmosphere to degass the reaction liquid. To this solution, 10 parts of 4-(methylthio) benzaldehyde represented by the following formula (34) was added dropwise, and the mixture was heated at 80° C. to start the reaction. After stirred for 30 minutes, the reaction liquid was cooled to 3° C., and precipitated crystals were collected by suction filtration. The collected solid was purified by recrystallization using a large amount of ethanol to obtain 7.6 parts of the target compound.

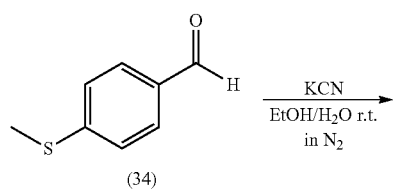

(34)

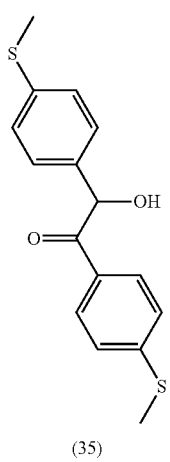

(35)

(Step 10) Synthesis of Intermediate Compound Represented by Formula (36)

The same procedure as in the step 1 was repeated except that the intermediate compound represented by the following formula (35) was used instead of the benzoin to obtain 6.3 parts of the intermediate compound represented by the following formula (36).

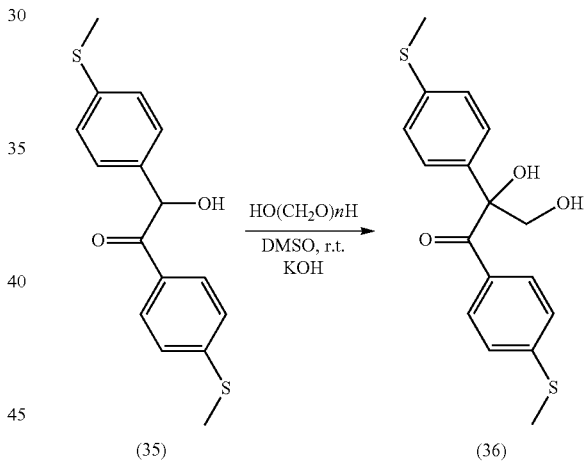

(Step 11) Synthesis of Compound of the Present Invention Represented by the Following Formula (A-5) (Photopolymerization Initiator 6)

1.0 part of the intermediate compound represented by formula (36) obtained in the step 10, 15 parts of toluene, and 0.3 part of triethylamine were added to a flask and stirred under reflux to homogeneity. Subsequently, 0.4 part of dicyclohexylmethane-4,4'-diisocyanate was added at room temperature. After stirring was continued for 12 hours, the solution was cooled, and the solvent was distilled off by an evaporator. The solution obtained was added dropwise to cyclohexane, and the mixture was washed by stirring for 30 minutes to obtain 1.0 part of the compound of the present invention represented by the following formula (A-5) (photopolymerization initiator 6).

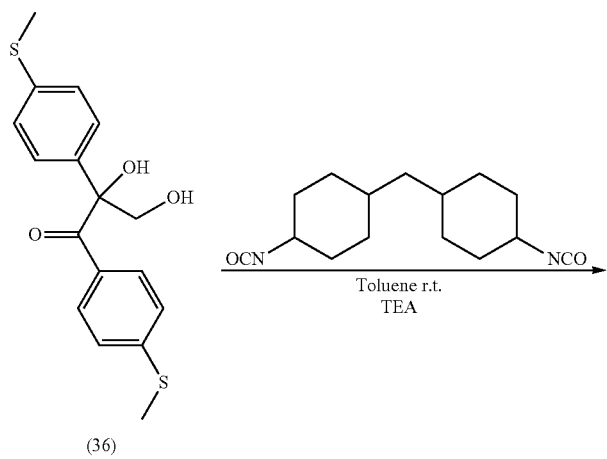

(36)

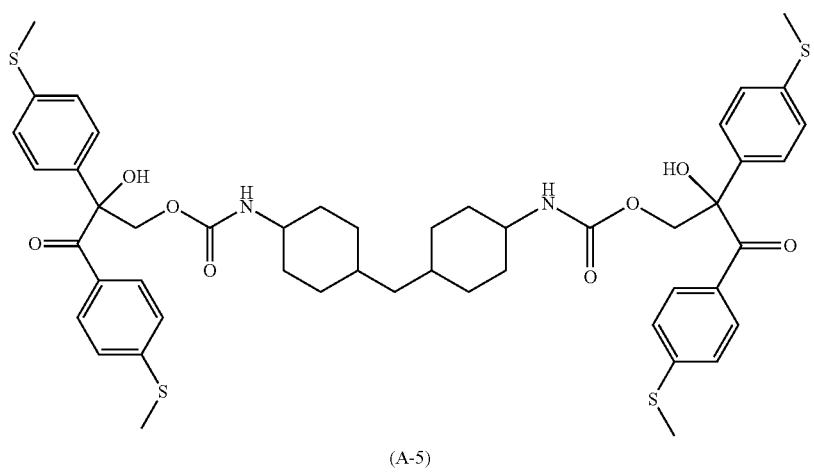

(A-5)

Example 7 Synthesis of Compound Represented by Formula (1) of the Present Invention (Step 12) Synthesis of Intermediate Compound Represented by Formula (38)

After 3.8 parts of sodium cyanide was dissolved by addition of 40 parts of water and 80 parts of ethanol, the solution was sonicated under nitrogen atmosphere to degass the reaction liquid. After 20 parts of 4-naphthaldehyde represented by the following formula (37) was added to this solution, the solution was refluxed under heating in an oil bath. After stirred for 30 minutes, the reaction liquid was cooled to room temperature, and the precipitated crystals were collected by suction filtration. The collected solid was purified by recrystallization using a large amount of ethanol to obtain 15 parts of the target compound.

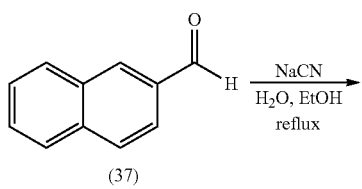

(37)

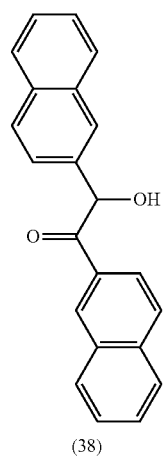

(38)

(Step 13) Synthesis of Intermediate Compound Represented by Formula (39)

The same procedure as in the step 1 was repeated except that the intermediate compound represented by the following formula (38) was used instead of the benzoin to obtain 12 parts of the intermediate compound represented by the following formula (39).

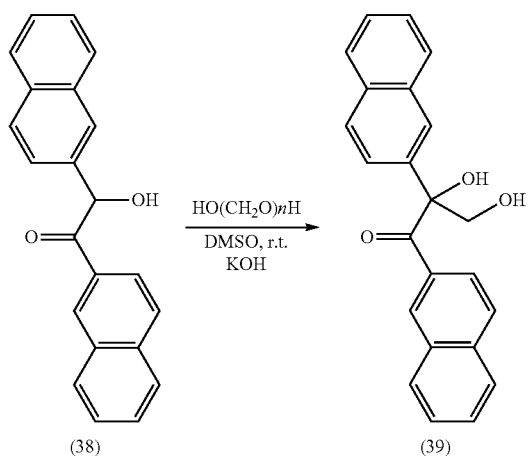 [SMILES: O=C(c1ccc2ccccc2c1)C(O)c1ccc2ccccc2c1 ; O=C(c1ccc2ccccc2c1)C(O)(CO)c1ccc2ccccc2c1]

(Step 14) Synthesis of Compound of the Present Invention Represented by the Following Formula (A-6) (Photopolymerization Initiator 7)

6.5 parts of the intermediate compound represented by formula (39) obtained in the step 13, 100 parts of toluene, and 0.06 part of tin octylate were added to a flask and stirred at 80° C. to homogeneity. Subsequently, 2.5 parts of dicyclohexylmethane-4,4'-diisocyanate was added at room temperature. After stirring was continued for 2 hours, the solution was cooled, and the solvent was distilled off by an evaporator. The solution obtained was added dropwise to cyclohexane, and the mixture was washed by stirring for 30 minutes to obtain 1.0 part of the compound of the present invention represented by the following formula (A-6) (photopolymerization initiator 7).

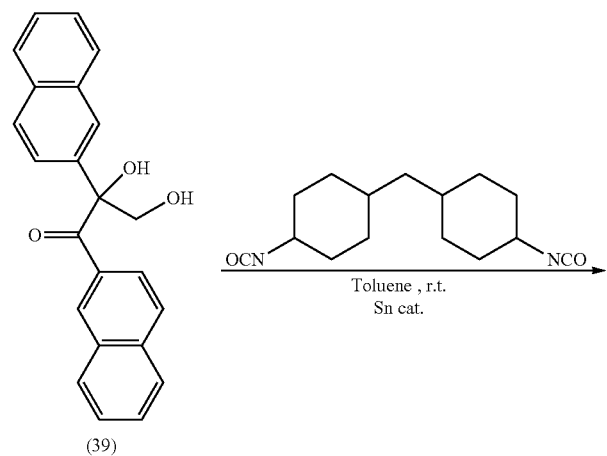

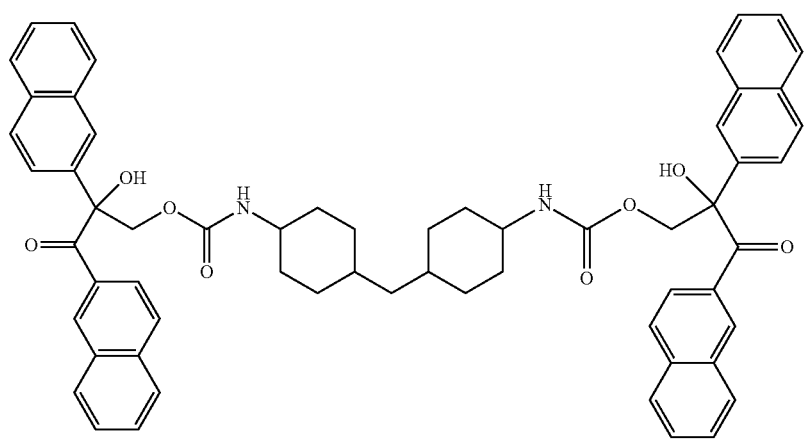

(Evaluation of Absorbance of Photopolymerization Initiator)

After 0.01 g of the photopolymerization initiator 1 obtained in Example 1 was dissolved in a small amount of THF, the solution was diluted with THF to 10 ml to obtain an initiator solution. Using a whole pipet, 1 ml of the initiator solution was collected, and the solution was again diluted with THF to 10 ml to thereby obtain an initiator diluted solution for the evaluation of absorbance. A quartz cell having an optical path length of 10 mm, filled with the initiator diluted solution obtained, was used to measure the absorbance of the photopolymerization initiator 1. Based on the measurement result of the absorbance, the molar extinction coefficient ε was calculated by the following expression. Also for the photopolymerization initiators 2, 5, 6, and 7 obtained respectively in Examples 2, 5, 6, and 7, the absorbance was measured, and the molar extinction coefficient s was calculated in the same manner as for the photopolymerization initiator 1. The measurement results of the absorbance are shown in FIG. 1, and the calculated values of the molar extinction coefficient ε are listed in Table 3.

Molar extinction coefficient ε=Absorbance/(Optical path length×Molar concentration of photopolymerization initiator)

TABLE 3

|  | Molar extinction coefficient (ε) | | |
| --- | --- | --- | --- |
|  | 313 nm | 365 nm | 405 nm |
| Photopolymerization initiator 1 | 427 | 253 | 87 |
| Photopolymerization initiator 2 | 779 | 24 | 8 |
| Photopolymerization initiator 5 | 415 | 70 | 19 |
| Photopolymerization initiator 6 | 27946 | 758 | 24 |
| Photopolymerization initiator 7 | 629 | 110 | 4 |

Examples 8 to 10

(Preparation of Photosensitive Resin Composition)

Respective components were mixed in accordance with the amounts to be blended listed in Table 4 to obtain photosensitive resin compositions.

TABLE 4

| Components | Product name | Solid content | Example 8 | Example 9 | Example 10 |
| --- | --- | --- | --- | --- | --- |
| Binder resin | CCR-1307H | 66.0% | 100 | 100 | 100 |
| Polyfunctional monomer | DPHA | 100.0% | 25 | 25 | 25 |
| Photopolymerization initiator | Photopolymerization initiator 1 (A-1) | 100.0% | 1.5 | | |
|  | Photopolymerization initiator 6 (A-5) | 100.0% | | 1.5 | |
|  | Photopolymerization initiator 7 (A-6) | 100.0% | | | 1.5 |
| Solvent | PGMEA | | | | |
| Solid content concentration | | 50 | | | |

Binder resin: CCR-1307H manufactured by NIPPON KAYAKU Co., Ltd.

Polyfunctional monomer: DPHA manufactured by NIPPON KAYAKU Co., Ltd.

Photopolymerization initiator 1: photopolymerization initiator 1 obtained in Example 1

Photopolymerization initiator 6: photopolymerization initiator 6 obtained in Example 6

Photopolymerization initiator 7: photopolymerization initiator 7 obtained in Example 7

Solvent: polyethylene glycol monomethyl ether acetate (PGMEA)

Evaluation of Remaining Film Ratio of Photosensitive Resin Composition

Figure 2:
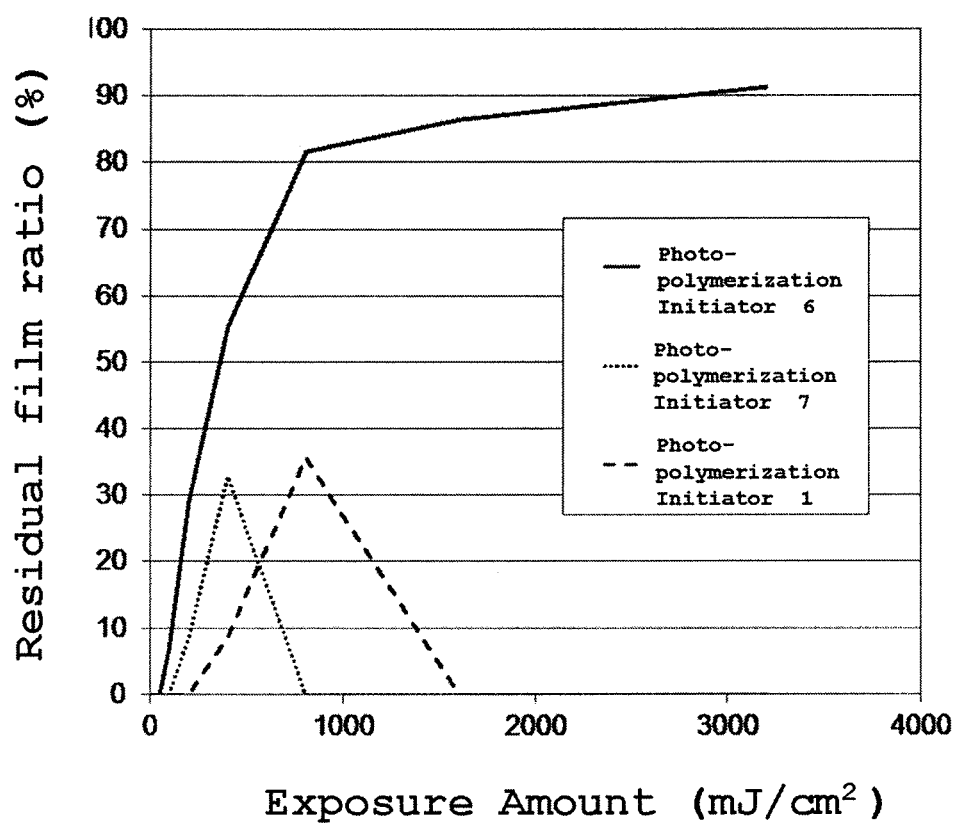
FIG. 2 shows the measurement results of the residual film rate of the photosensitive resin composition of the present invention.

The photosensitive resin compositions of Examples 8 to 10 were cured and developed under the evaluation conditions listed in Table 5. The film thickness after development was measured by a probe-type film thickness measurement instrument to evaluate the remaining film ratio at each amount of exposure (the thickness of a pattern obtained after development when the film thickness before exposure was assumed to be 1), and the results are shown in FIG. 2. Note that the amount of exposure is the amount of exposure measured at a wavelength of 365 nm.

TABLE 5

| Evaluation conditions of photosensitive resin compositions | | | | |
| --- | --- | --- | --- | --- |
|  |  | Example 8 | Example 9 | Example 10 |
| Evaluation conditions | Drying temperature | 110° C. × 1 min | | |
|  | Exposure conditions | High-pressure mercury lamp (313 nm -) | | |
|  | Heating conditions | 110° C. × 5 min | | |
| Evaluation results | Development | 23° C., PGMEA 30 sec | | |

INDUSTRIAL APPLICABILITY

The photosensitive resin composition of the present invention provides excellent image resolution, sensitivity, and storage stability. In addition, cured products of the resin composition, which have excellent thermal stability, are useful in fields where corrosion resistance of metal substrates is required.

The invention claimed is:
1. A compound of formula (1):

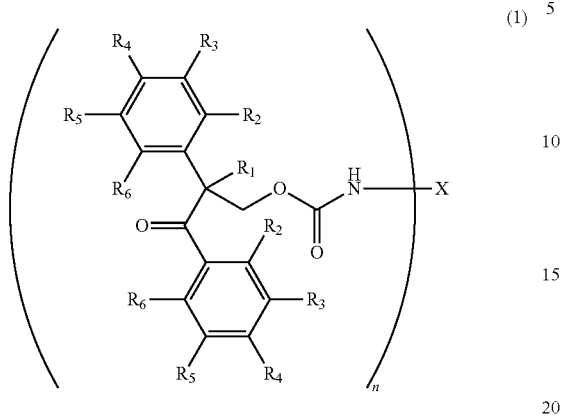

wherein in formula (1), $R_1$ is a hydrogen atom, a hydroxyl group, an alkoxy group having a carbon number of 1 to 18 or an organic group selected from the group consisting of an alkyl group having a carbon number of 1 to 18, an alkenyl group having a carbon number of 2 to 18, an alkynyl group having a carbon number of 2 to 18, an aryl group having a carbon number of 6 to 12, an acyl group having a carbon number 1 to 18, an aroyl group having a carbon number of 7 to 18, a nitro group, a cyano group, an alkylthio group having a carbon number of 1 to 18, and a halogen atom, when there is a plurality of $R_1$, each $R_1$ may be the same or different from each other;

$R_2$, $R_3$, $R_5$, and $R_6$ each independently is a hydrogen atom, a halogen atom, a hydroxyl group, an alkoxy group having a carbon number of 1 to 18, a mercapto group, a sulfide group, a silyl group, a silanol group, a nitro group, a nitroso group, a cyano group, a sulfino group, a sulfo group, a sulfonato group, a phosphino group, a phosphinyl group, a phosphono group, a phosphonato group, an amino group, an ammonio group, or an organic group selected from the group consisting of an alkyl group having a carbon number of 1 to 20, an aryl group having a carbon number of 6 to 20, an aralkyl group, a halogenated alkyl group, an isocyano group, a cyanate group, an isocyanato group, a thiocyanato group, an isothiocyanato group, an alkoxycarbonyl group, a carbamoyl group, a thiocarbamoyl group, a carboxyl group, a carboxylate group, an acyl group having a carbon number of 1 to 20, an acyloxy group, and a hydroxyimino group;

$R_2$ and $R_3$ on the same benzene ring may be connected to form a ring structure;

$R_5$ and $R_6$ on the same benzene ring may be connected to form a ring structure;

$R_4$ each independently is an organic group selected from the group consisting of an alkyl group having a carbon number of 1 to 20 containing a thioether bond, an aryl group having a carbon number of 6 to 20 containing a thioether bond, an aralkyl group containing a thioether bond, a halogenated alkyl group containing a thioether bond, an isocyano group containing a thioether bond, a cyanate group containing a thioether bond, an isocyanato group containing a thioether bond, a thiocyanato group containing a thioether bond, an isothiocyanato group containing a thioether bond, an alkoxycarbonyl group containing a thioether bond, a carbamoyl group containing a thioether bond, a thiocarbamoyl group containing a thioether bond, a carboxyl group containing a thioether bond, a carboxylate group containing a thioether bond, an acyl group containing a thioether bond, an acyloxy group having an acyl group containing a thioether bond, and a hydroxyimino group containing a thioether bond;

X is a residue being a saturated hydrocarbon including a ring structure having a 3- to 10-membered ring from which n hydrogen atoms are removed; and n is an integer of 1 to 6.

2. The compound according to claim 1, wherein the organic group of $R_4$ is an alkyl group having a carbon number of 1 to 20 containing a thioether bond or an aryl group having a carbon number of 6 to 20 containing a thioether bond.

3. The compound according to claim 1, wherein the compound has the structure of formula (2):

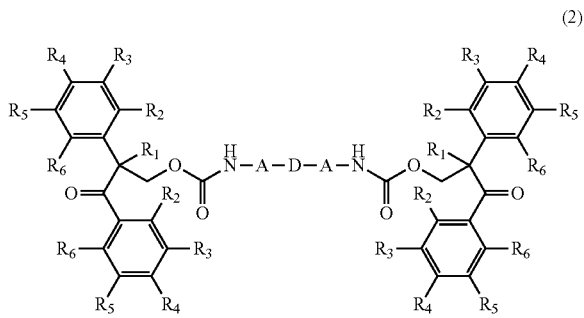

wherein in formula (2), $R_1$ to $R_6$ are the same as $R_1$ to $R_6$ in formula (1);

A is a cycloalkylene group which is a saturated cyclic hydrocarbon from which two hydrogen atoms are removed, and which is selected from the group consisting of a cyclopropane ring, a cyclobutane ring, a cyclopentane ring, a cyclohexane ring, and a cycloadamantane ring; and D is an alkylene group having a carbon number of 1 to 18.

4. The compound according to claim 3, wherein the compound has the structure of formula (3):

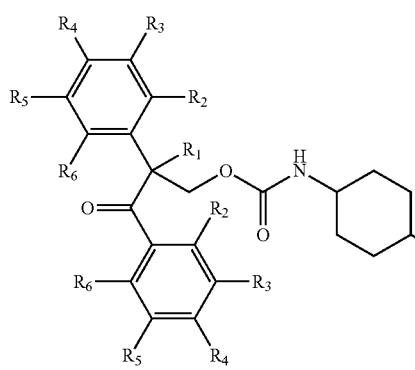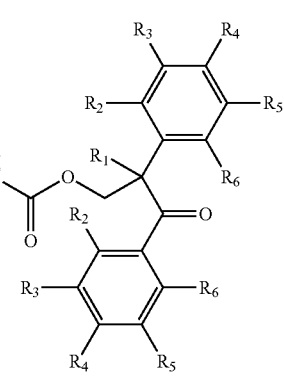

(3)

wherein in formula (3), $R_1$ to $R_6$ are the same as $R_1$ to $R_6$ in formula (2).

5. The compound according to claim 1, wherein $R_1$ is a hydroxyl group.

6. A photopolymerization initiator comprising the compound according to claim 1.

7. A photosensitive resin composition comprising a polymer precursor capable of being polymerized by irradiation or by both of irradiation and heating in the presence of a photopolymerization initiator, and the photopolymerization initiator according to claim 6.

8. The photosensitive resin composition according to claim 7, wherein the polymer precursor comprises at least one selected from the group consisting of a compound having a substituent selected from the group consisting of an epoxy group, an isocyanate group, an oxetane group, an acryloyl group, a methacryloyl group, a maleimide group, and a thiirane group; a polysiloxane precursor; a polyimide precursor; and a polybenzoxazole precursor.

9. The photosensitive resin composition according to claim 8, wherein the polymer precursor comprises a compound having an epoxy group.

10. A method for forming a pattern comprising:
changing solubility of an irradiation area by irradiation to a coat, a film or a formed body of the photosensitive resin composition according to claim 7 in a predefined pattern, followed by heating or on heating; and
removing a non-irradiated area by performing development.

* * * * *